US008080632B2

(12) United States Patent
Roth

(10) Patent No.: US 8,080,632 B2
(45) Date of Patent: Dec. 20, 2011

(54) PEPTIDE MIMICS OF MELANOCYTE STIMULATING HORMONE

(75) Inventor: Jesse Roth, Whitestone, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 396 days.

(21) Appl. No.: 11/991,121

(22) PCT Filed: Sep. 1, 2006

(86) PCT No.: PCT/US2006/034054
§ 371 (c)(1),
(2), (4) Date: Jan. 13, 2009

(87) PCT Pub. No.: WO2007/027910
PCT Pub. Date: Mar. 8, 2007

(65) Prior Publication Data
US 2010/0048465 A1 Feb. 25, 2010

Related U.S. Application Data

(60) Provisional application No. 60/713,927, filed on Sep. 1, 2005.

(51) Int. Cl.
*C07K 14/245* (2006.01)
(52) U.S. Cl. ....................................................... 530/324
(58) Field of Classification Search ........................ None
See application file for complete search history.

(56) References Cited

U.S. PATENT DOCUMENTS
2004/0241715 A1 12/2004 Zyskind et al.

FOREIGN PATENT DOCUMENTS
| WO | WO 99/01020 | 1/1999 |
| WO | WO 01/75067 | 10/2001 |
| WO | WO 01/90304 | 11/2001 |

OTHER PUBLICATIONS

Skar et al. (Biochem. 14(17): 3922-3926, 1975).*
Catania, et al. "Targeting Melanocortin Receptors as a Novel Strategy to Control Inflammation." Pharmacological Reviews, 56:1 (2004), pp. 1-29.
Basset, et al. "Innate Immunity and Pathogen—Host Interaction." Vaccine, 21:2 ( 2003), pp. S12-S23.
Goodfellow, et al. "The Melanocortin System and its Role in Obesity and Cachexia." Current Topics in Medicinal Chemistry, 3:8 (2003), pp. 855-883.
The International Search Report for PCT Application No. PCT/US2006/034054, dated Dec. 26, 2007.
The Written Opinion of the Interternational Searching Authority for PCT Application No. PCT/US2006/034054, dated Dec. 26, 2007.
The Supplemental European Search Report dated Oct. 2, 2009 for European Application No. 06814008.6.
The Communication dated Oct. 28, 2009 for European Application No. 06814008.6.
Hsiao et al. "The Microbes of the Intestine: An Introduction to Their Metabolic and Signaling Capabilities." Endoc. & Metabol. Clin. of North America 37:4, Dec. 2008.

* cited by examiner

*Primary Examiner* — Christine J Saoud
(74) *Attorney, Agent, or Firm* — Amster, Rothstein & Ebenstein, LLP

(57) ABSTRACT

Provided are peptides having melanocyte stimulating hormone activity. Also provided are vectors encoding these peptides and transgenic cells comprising the above vectors. Additionally, methods of reducing or preventing release of an inflammatory cytokine from mammalian cells are provided, as are methods for treating a mammal suffering from, or at risk for, a condition mediated by an inflammatory cytokine cascade. Further provided are methods of reducing levels of an inflammatory cytokine in a mammal, methods of treating an overweight mammal, methods of decreasing food intake in a mammal and methods of inhibiting innate immunity in the digestive system of a mammal.

7 Claims, 16 Drawing Sheets

| | | Identities | Positives | Score E-value |
|---|---|---|---|---|
| MECO-1 (1-33): | $^{671}$SLTKGRASYTMEFLKYDEAPSNVAQAVIEARGK$^{703}$ | | | |
| EFG_(Q83JC3): [Shigella flexneri] | $^{671}$SLTKGRASYTMEFLKYDEAPSNVAQAVIEARGK$^{703}$ SLTKGRASYTMEFLKYDEAPSNVAQAVIEARGK | 33/33 (100%) | 33/33 (100%) | 106 5e-23 |
| EFG_(P0A1H3): [Salmonella typhimurium] | $^{671}$SLTKGRASYTMEFLKYDDAPNNVAQAVIEARGK$^{703}$ SLTKGRASYTMEFLKYD+AP NVAQAVIEARGK | 31/33 (93%) | 32/33 (96%) | 101 2e-21 |
| EFG_(Q6C2W5): [Erwinia carotovora] | $^{672}$SLTKGRASYSMEFLKYDDAPNNVAQAVIEARGK$^{704}$ SLTKGRASY MEFLKYD+AP NVAQAVIEARGK | 30/33 (90%) | 31/33 (93%) | 98.2 1e-20 |
| EFG_(Q7N9B2): [Photorhabdus luminescens] | $^{669}$SQTQGRASYSMEFLKYNEAPSNVAQAIIEAR$^{699}$ S T GRASY MEFLKY+ EAPSNVAQA+IEAR | 26/31 (83%) | 28/31 (89%) | 83.8 3e-16 |
| EFG_(Q664R6): [Yersinia pseudotuberculosis] | $^{670}$SQTQGRASYSMEFLEYAEAPSNVAKAVIEARGK$^{702}$ S T GRASY MEFL Y EAPSNVA AVIEARGK | 27/33 (81%) | 27/33 (81%) | 80.0 4e-15 |
| EFG_(Q83ES7): [Coxiella burnetii] | $^{668}$SLSQGRATYTMEFLKYAEAPSNIAEAII$^{695}$ SL GRA YTMEFLKY EAPSN+A+A+I | 21/28 (75%) | 24/28 (85%) | 69.8 5e-12 |
| EFG_(Q7VTD5): [Bordetella pertussis] | $^{668}$SLTQGRATYTMEF-KHYAEAPKNVADEVIAARGK$^{700}$ SLT GRA YTMEF K Y EAP NVA VI ARGK | 25/34 (73%) | 25/34 (73%) | 67.2 3e-11 |
| EFG_(P57938): [Pasteurella multocida] | $^{668}$SQTQGRASYSMEPLKYAEAPKNVADAIIEAR$^{698}$ S T GRASY ME LKY EAP NVA A+IEAR | 23/31 (74%) | 24/31 (77%) | 65.1 1e-10 |
| EFG_(Q7VRN9): [Candidatus Blochmannia floridanus] | $^{676}$SQTQGRASHSMEFLKYNEVPNNIAQSIIESR$^{706}$ S T GRAS MEFLKY+E P N+AQ +IE R | 20/31 (64%) | 23/31 (73%) | 65.1 1e-11 |
| EFG_(Q65W89): [Mannheimia succiniciproducens] | $^{660}$SQTQGRASYSMEPLKYAEAPTSVAAAVIEAR$^{698}$ S T GRASY ME LKY EAP VA AVIEAR | 23/31 (74%) | 23/31 (74%) | 64.7 2e-10 |
| EFG_(Q5L9B1): [Bacteroides fragilis] | $^{681}$SLTGGRASFIMKFASYELVPSDV$^{703}$ SLT GRAS+ M F Y+ PS+V | 13/23 (56%) | 16/23 (69%) | 32.5 1.2 |
| EFG_(Q8A5S1): [Bacteroides thetaiotaomicron] | $^{681}$SLTGGRASFIMKFASYELVPTDV$^{703}$ SLT GRAS+ M F Y+ P +V | 12/23 (52%) | 15/223 (65%) | 29.9 6.9 |

C

PEPTIDE MIMICS OF MELANOCYTE STIMULATING HORMONE

CROSS-REFERENCE TO RELATED APPLICATION

This is a U.S. national phase of PCT Application No. PCT/EP2006/034054, filed Sep. 1, 2006, which claims the benefit of U.S. Provisional Application No. 60/713,927, filed Sep. 1, 2005.

BACKGROUND OF THE INVENTION (1) Field of the Invention

The present invention generally relates to bioactive peptides. More specifically, the invention is directed to peptides that mimic melanocyte stimulating hormone by activating mammalian melanocortin receptors.

(2) Description of the Related Art

References Cited

Abreu M T, Fukata M, Arditi M. TLR signaling in the gut in health and disease. J. Immunol. 2005 Apr. 15; 174(8):4453-60.

Backhed F, Ley R E, Sonnenburg J L, Peterson D A, Gordon J I. Host-bacterial mutualism in the human intestine. Science. 2005 Mar. 25; 307(5717):1915-20.

Badman M K, Flier J S. The gut and energy balance: visceral allies in the obesity wars. Science. 2005 Mar. 25; 307(5717):1909-14.

Bardwell L. A walk-through of the yeast mating pheromone response pathway. Peptides. 2004 September; 25(9):1465-76. Review. Erratum in: Peptides. 2005 February; 26(2):337. Corrected and republished in: Peptides. 2005 February; 26(2):339-50.

Bhargava K, Templeton P, Spremulli L L. Expression and characterization of isoform 1 of human mitochondrial elongation factor G. Protein Expr Purif. 2004 October; 37(2):368-76.

Catania A, Delgado R, Airaghi L, Cutuli M, Garofalo L, Carlin A, Demitri M T, Lipton J M. α-MSH in systemic inflammation. Central and peripheral actions. Ann N Y Acad. Sci. 1999 Oct. 20; 885:183-7.

Catania A, Gatti S, Colombo G, Lipton J M. Targeting melanocortin receptors as a novel strategy to control inflammation. Pharmacol Rev. 2004 March; 56(1): 1-29.

Chai B X, Neubig R R, Millhauser G L, Thompson D A, Jackson P J, Barsh G S, Dickinson C J, Li J Y, Lai Y M, Gantz I. Inverse agonist activity of agouti and agouti-related protein. Peptides. 2003 April; 24(4):603-9.

Chandran P, Satthaporn S, Robins A, Eremin O. Inflammatory bowel disease: dysfunction of GALT and gut bacterial flora (I). Surgeon. 2003 April; 1(2):63-75.

Chhajlani V, Wikberg J E. Molecular cloning and expression of the human melanocyte stimulating hormone receptor cDNA (FEBS 11553). FEBS Lett. 1996 Jul. 22; 390(2):238.

Cone, R. D. (Ed) (2000). The Melanocortin Receptors. Humana Press Totowa, N.J., USA 551 pp.

Damcott C M, Sack P, Shuldiner A R. The genetics of obesity. Endocrinol Metab Clin North Am. 2003 December; 32(4):761-86.

Delgado R, Carlin A, Airaghi L, Demitri M T, Meda L, Galimberti D, Baron P, Lipton J M, Catania A. Melanocortin peptides inhibit production of proinflammatory cytokines and nitric oxide by activated microglia. J Leukoc Biol. 1998 June; 63(6):740-5.

Dumitriu I E, Baruah P, Manfredi A A, Bianchi M E, Rovere-Querini P. HMGB1: guiding immunity from within. Trends Immunol. 2005 July; 26(7):381-7.

Eberle, A. N. 2000 Propiomelanocortin and the Melanocortin Peptides. In The Melanocortin Receptors. R. D. Cone, editor. Humana Press, Totowa, N.J., USA. 3-67.

Eckburg P B, Bik E M, Bernstein C N, Purdom E, Dethlefsen L, Sargent M, Gill S R, Nelson K E, Relman D A. Diversity of the human intestinal microbial flora. Science. 2005 Jun. 10; 308(5728):1635-8.

Eckmann L. Innate immunity and mucosal bacterial interactions in the intestine. Curr Opin Gastroenterol. 2004 March; 20(2):82-8.

Farooqi I S, O'Rahilly S. Monogenic obesity in humans. Annu Rev Med. 2005; 56:443-58.

Federle M J, Bassler B L. Interspecies communication in bacteria. J Clin Invest. 2003 November; 112(9):1291-9.

Gallio M, Sturgill G, Rather P, Kylsten P. A conserved mechanism for extracellular signaling in eukaryotes and prokaryotes. Proc Natl Acad Sci USA. 2002 Sep. 17; 99(19):12208-13.

Gao J, Yu L, Zhang P, Jiang J, Chen J, Peng J, Wei Y, Zhao S. Cloning and characterization of human and mouse mitochondrial elongation factor G, GFM and Gfm, and mapping of GFM to human chromosome 3q25.1-q26.2. Genomics. 2001 May 15; 74(1):109-14.

Garside P, Millington O, Smith K M. The anatomy of mucosal immune responses. Ann NY Acad. Sci. 2004 December; 1029:9-15.

Gebbers J O, Laissue J A. Bacterial translocation in the normal human appendix parallels the development of the local immune system. Ann N Y Acad. Sci. 2004 December; 1029:337-43.

Gerst J E, Sole J, Hazum E, Salomon Y. Identification and characterization of melanotropin binding proteins from M2R melanoma cells by covalent photoaffinity labeling. Endocrinology. 1988 October; 123(4):1792-7.

Getz G S. Thematic review series: the immune system and atherogenesis. Immune function in atherogenesis. J Lipid Res. 2005 January; 46(I):1-10.

Greenberg E P. Bacterial communication and group behavior. J Clin Invest. 2003 November; 112(9): 1288-90.

Hammarsund M, Wilson W, Corcoran M, Merup M, Einhorn S, Grander D, Sangfelt O. Identification and characterization of two novel human mitochondrial elongation factor genes, hEFG2 and hEFG1, phylogenetically conserved through evolution. Hum Genet. 2001 November; 109(5):542-50.

Hansson G K. Inflammation, atherosclerosis, and coronary artery disease. N Engl J Med. 2005 Apr. 21; 352(16):1685-95.

Haynes R C Jr, Sutherland E W, Rall T W. The role of cyclic adenylic acid in hormone action. Recent Prog Horm Res. 1960; 16:121-38.

Henke J M, Bassler B L. Bacterial social engagements. Trends Cell Biol. 2004 November; 14(11):648-56.

Hoebe K, Janssen E, Beutler B. The interface between innate and adaptive immunity. Nat. Immunol. 2004:5(10): 971-4.

Hruby, V. J. and Han G. 2000 The Molecular Pharmacology of A-Melanocyte Stimulating Hormone Structure-Activity Relationships for Melanotropins at Melanocortin Receptors. In The Melanocortin Receptors. R. D. Cone, editor. Humana Press, Totowa, N.J., USA. 239-261.

Janeway C A Jr, Medzhitov R. Innate immune recognition. Annu Rev Immunol. 2002; 20:197-216.

Kieber-Emmons et al., Curr. Opin. Biotechnol. 1997; 8:435-441.

Kita T, Inoue A, Nakanishi S, Numa S. Purification and characterization of the messenger RNA coding for bovine corticotropin/beta-lipotropin precursor. Eur J Biochem. 1979 Jan. 15; 93(2):213-20.

Korner J, Leibel R L. To eat or not to eat—how the gut talks to the brain. N Engl J Med. 2003 Sep. 4; 349(10):926-8.

Krude H, Biebermann H, Luck W, Horn R, Brabant G, Gruters A. Severe early-onset obesity, adrenal insufficiency and red hair pigmentation caused by POMC mutations in humans. Nat. Genet. 1998 June; 19(2):155-7.

Lefkowitz R J, Roth J, Pricer W, Pastan I. ACTH receptors in the adrenal: specific binding of ACTH-125I and its relation to adenyl cyclase. Proc Natl Acad Sci USA. 1970 March; 65(3):745-52.

Lenard J. Mammalian hormones in microbial cells. Trends Biochem Sci. 1992 April; 17(4): 147-50.

Lerner A B. The discovery of the melanotropins. A history of pituitary endocrinology. Ann N Y Acad. Sci. 1993 May 31; 680:1-12.

LeRoith D, Delahunty G, Wilson G L, Roberts C T Jr, Shemer J, Hart C, Lesniak M A, Shiloach J, Roth J. Evolutionary aspects of the endocrine and nervous systems. Recent Prog Horm Res. 1986; 42:549-87.

Li J, Kokkola R, Tabibzadeh S, Yang R, Ocliani M, Qiang X, Harris H E, Czura C J, Wang H, Ulloa L. Wang H, Warren H S, Moldawer L L, Fink M P, Andersson U, Tracey K J, Yang H. Structural basis for the proinflammatory cytokine activity of high mobility group box 1. Mol. Med. 2003 January-February; 9(1-2):37-45.

Li J, Wang H, Mason J M, Levine J, Yu M, Ulloa L, Czura C J, Tracey K J, Yang H. Recombinant HMGB1 with cytokine-stimulating activity. J Immunol Methods. 2004 June; 289 (1-2):211-23.

Lipton J M, Macaluso A, Hiltz M E, Catania A. Central administration of the peptide α-MSH inhibits inflammation in the skin. Peptides. 1991 July-August; 12(4):795-8.

Lotze M T, Tracey K J. High-mobility group box 1 protein (HMGB1): nuclear weapon in the immune arsenal. Nat Rev Immunol. 2005 April; 5(4):331-42.

Maaser C, Kannengiesser K, Specht C, Luegering A, Brzoska T, Luger T A, Domschke W, Kucharzik T. Crucial role of the melanlocortin receptor MC1R in experimental colitis. Gut. 2006 Mar. 16; [Epub ahead of print] PMID: 16543288.

Macchia V, Bates R W, Pastan I. The purification and properties of a thyroid-stimulating factor isolated from *Clostridium perfringens*. J Biol Chem. 1967 Aug. 25; 242 (16):3726-30.

Macdonald T T, Monteleone G. Immunity, inflammation, and allergy in the gut. Science. 2005 Mar. 25; 307(5717): 1920-5.

Mains R E, Eipper B A, Ling N. Common precursor to corticotropins and endorphins. Proc Natl Acad Sci USA. 1977 July; 74(7):3014-8.

Merritt, H. H. 1955 A textbook of neurology. Lea & Febiger. Philadelphia, U.S.A. 746 pp (see p. 47)

Mathesius U, Mulders S, Gao M, Teplitski M, Caetano-Anolles G, Rolfe B G, Bauer W D. Extensive and specific responses of a eukaryote to bacterial quorum-sensing signals. Proc Natl Acad Sci USA. 2003 Feb. 4; 100(3):1444-9.

McGeer P L, McGeer E G. Inflammation and the degenerative diseases of aging. Ann N Y Acad. Sci. 2004 December; 1035:104-16.

Mountjoy K G, Robbins L S, Mortrud M T, Cone R D. The cloning of a family of genes that encode the melanocortin receptors. Science. 1992 Aug. 28; 257(5074):1248-51.

Pasare C, Medzliitov R. Toll-like receptors: linking innate and adaptive immunity. Microbes Infect. 2004 December; 6(15): 1382-7.

Rendon-Mitchell B, Ochani M, Li J, Han J, Wang H, Yang H, Susarla S, Czura C, Mitchell R A, Chen G, Sama A E, Tracey K J, Wang H. IFN-gamma induces high mobility group box I protein release partly through a TNF-dependent mechanism. J. Immunol. 2003 Apr. 1; 170(7):3890-7.

Rielil R M, Toft D O. Analysis of the steroid receptor of *Achlya* ambisexualis. J Biol Chem. 1984 Dec. 25; 259(24): 15324-30.

Ripka et al., Curr. Opin. Chem. Biol. 1998; 2:441-452.

Roberts J L, Herbert E. Characterization of a common precursor to corticotropin and beta-lipotropin: cell-free synthesis of the precursor and identification of corticotropin peptides in the molecule. Proc Natl Acad Sci USA. 1977 November; 74(11):4826-30.

Roth J, Leroith D, Collier E S, Watkinson A, Lesniak M A. The evolutionary origins of intercellular communication and the Maginot Lines of the mind. Ann N Y Acad. Sci. 1986; 463:1-11.

Saez J M, Evain D, Gallet D. Role of cyclic AMP and protein kinase on the steroidogenic action of ACTH, prostaglandin E1 and dibutyryl cyclic AMP in normal adrenal cells and adrenal tumor cells from humans. J Cyclic Nucleotide Res. 1978 August; 4(4):311-21.

Sanchez-Mas J, Hahmann C, Gerritsen I, Garcia-Borron J C, Jimenez-Cervantes C. Agonist-independent, high constitutive activity of the human melanocortin I receptor. Pigment Cell Res. 2004 August; 17(4):386-95.

Sanderson, Med. Res. Rev. 1999; 19:179-197.

Sartor R B. Review article: Role of the enteric microflora in the pathogenesis of intestinal inflammation and arthritis. Aliment Pharmacol Ther. 1997 December; 11 Suppl 3:17-22; discussion 22-3.

Sartor R B. Targeting enteric bacteria in treatment of inflammatory bowel diseases: why, how, and when. Curr Opin Gastroenterol. 2003 July; 19(4):358-65.

Schimmer B P, Ueda K, Sato G H. Site of action of adrenocorticotropic hormone (ACTH) in adrenal cell cultures. Biochem Biophys Res Commun. 1968 Sep. 6; 32(5):806-10.

Smith D W, Nagler-Anderson C. Preventing intolerance: the induction of nonresponsiveness to dietary and microbial antigens in the intestinal mucosa. J Immunol. 2005 Apr. 1; 174(7):3851-7.

Smythies L E, Sellers M, Clements R, Mosteller-Barnum M, Meng G, Benjamin W, Orenstein J M, Smith P. Human intestinal macrophages display profound inflammatory anergy despite avid phagocytic and bacteriocidal activity. J Clin Invest. 2005 January; 115(1):66-75.

Steinhoff U. Who controls the crowd? New findings and old questions about the intestinal microflora. Immunol Lett. 2005 Jun. 15; 99(1):12-6. Epub 2005 Jan. 21.

Taherzadeh S, Sharma S, Chhajlani V, Gantz I, Rajora N, Demitri M T, Kelly L, Zhao H. Ichiyama T, Catania A, Lipton J M. A-MSH and its receptors in regulation of tumor necrosis factor-α production by human monocyte/macrophages. Am J. Physiol. 1999 May; 276(5 Pt 2):R1289-94.

Taunton O D, Roth J, Pastan I. The first step in ACTH action: binding to tissue. J Clin Invest. 1967 June; 46(6): 1122-1129.

Thompson J D, Higgins D G, Gibson T J. CLUSTAL W: improving the sensitivity of progressive multiple sequence alignment through sequence weighting, position-specific gap penalties and weight matrix choice. Nucleic Acids Res. 1994 Nov. 11; 22(22):4673-80.

Schuiling G A. Deceive, and be deceived! J Psychosom Obstet. Gynaecol. 2004 June; 25(2): 170-4.

Urban S, Freeman M. Intramembrane proteolysis controls diverse signalling pathways throughout evolution. Curr Opin Genet Dev. 2002 October; 12(5):512-8.

Vaisse C, Clement K, Guy-Grand B, Froguel P. A frameshift mutation in human MC4R is associated with a dominant form of obesity. Nat. Genet. 1998 October; 20(2):113-4.

Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J. HMG-1 as a late mediator of endotoxin lethality in mice. Science. 1999 Jul. 9; 285(5425):248-51.

Wang H, Yang H, Tracey K J. Extracellular role of HMGB1 in inflammation and sepsis. J Intern Med. 2004 March; 255 (3):320-31.

Wichmann M W, Haisken J M, Ayala A, Chaudry I H. Melatonin administration following hemorrhagic shock decreases mortality from subsequent septic challenge. J Surg Res. 1996 October; 65(2):109-14.

Wilson C J, Finch C E, Cohen H J. Cytokines and cognition—the case for a head-to-toe inflammatory paradigm. J Am Geriatr Soc. 2002 December; 50(12):2041-56.

Yaffe K, Kanaya A, Lindquist K, Simonsick E M, Harris T, Shorr R I, Tylavsky F A, Newman A B. The metabolic syndrome, inflammation, and risk of cognitivedecline. JAMA. 2004 Nov. 10; 292(18):2237-42.

Yang H, Ochani M, Li J, Qiang X, Tanovic M, Harris H E, Susarla S M, Ulloa L, Wang H, DiRaimo R, Czura C J, Wang H, Roth J, Warren H S, Fink M P, Fenton M J, Andersson U, Tracey K J. Reversing established sepsis with antagonists of endogenous high-mobility group box 1. Proc Natl Acad Sci USA. 2004 Jan. 6; 101(1):296-301.

Yang H, Wang H, Czura C J, Tracey K J. The cytokine activity of HMGB1. J Leukoc Biol. 2005 July; 78(1):1-8. Epub 2005 Feb. 25.

Yeo G S, Farooqi I S, Aminian S, Halsall D J, Stanhope R G, O'Rahilly S. A frameshift mutation in MC4R associated with dominantly inherited human obesity. Nat. Genet. 1998 October; 20(2):111-2.

How does the innate immune system keep silent in the presence of the bacteria that reside normally in the host's intestinal tract (Janeway and Medzhitov, 2002; Steinhoff, 2005; Smith and Nagler-Anderson, 2005)? Among nature's densest collections of cells, these microbes are metabolizing continuously and proliferating (Eckburg et al., 2005; Backhed et al., 2005; Chandran et al., 2003). They are also very near to the body's largest lymphoid organ, the gut associated lymphoid tissue (GALT) (Chandran et al., 2003). The innate immune system, with sets of specific receptors, is continuously on the alert to recognize as well as respond promptly and vigorously to bacteria, alive or dead, as well as to molecular components of bacteria (Pasare and Bedzhitov, 2004; Hoebe et al., 2005; Macdonald and Monteleone, 2005; Abreu et al., 2005). Minute amounts of bacterial products typically activate the innate immune system's cellular and humoral responses designed to combat bacteria. Sometimes these responses may be so vigorous that they kill the host that is being defended.

We hypothesize that *E. coli* and other organisms in the flora of the intestine release substances that act via host cell receptors of hormones or hormone-like agents to maintain the normal quiescent state whereby the vast biomass of microorganisms in the intestinal tract (existing at the highest density of cells in any known ecosystem) live in biological peace in the GI tract (dubbed by us pax intestinalis). By contrast, minute numbers of such organisms in blood or other body cavities typically activate rapidly multiple pathways of the innate immune system to generate a wide range of chemical and humoral responses (Janeway and Medzhitov, 2002; Steinhoff, 2005; Smith and Nagler-Anderson, 2005; Eckburg et al., 2005; Backhed et al., 2005; Chandran et al., 2003; Pasare and Bedzhitov, 2004; Hoebe et al., 2005; Macdonald and Monteleone, 2005; Abreu et al., 2005). Identification and characterization of these hypothesized substances are desirable to characterize bacterial mechanisms to escape mammalian immunity, and to develop treatments for diseases characterized by excessive reactions, such as inflammatory cytokine cascades. The present invention addresses that need.

SUMMARY OF THE INVENTION

Accordingly, the inventors have identified peptides that mimic melanocyte stimulating hormones by activating mammalian melanocortin receptors, and inhibiting release of proinflammatory cytokines. The peptides are effective treatments for septic shock and other conditions entailing activation of inflammatory cytokine cascades.

Thus, in some embodiments, the invention is directed to isolated and purified peptides of less than 680 amino acids or mimetics. The peptides comprise 33 amino acids or mimetics of a naturally occurring elongation factor-G corresponding to amino acids 671-703 of elongation factor-G (EF-G) of *E. coli*, having SEQ ID NO:14.

In other embodiments, the invention is directed to isolated and purified peptides of less than 680 amino acids or mimetics. The peptides comprise 33 amino acids or mimetics having SEQ ID NO:2

The invention is additionally directed to vectors encoding the above peptides.

In further embodiments, the invention is directed to transgenic cells comprising the above vectors.

The invention is also directed to methods of reducing or preventing release of an inflammatory cytokine from a mammalian cell. The methods comprise contacting the cell with any of the above peptides that activate a mammalian melanocortin receptor, in a manner sufficient to reduce or prevent release of the inflammatory cytokine.

In additional embodiments, the invention is directed to methods for treating a mammal suffering from a condition mediated by an inflammatory cytokine cascade. The methods comprise administering to the mammal any of the above peptides that activate a mammalian melanocortin receptor, in a manner sufficient to reduce the inflammatory cytokine cascade.

The invention is further directed to methods for treating a mammal at risk for a condition mediated by an inflammatory cytokine cascade. The methods comprise administering to the mammal any of the above peptides that activate a mammalian melanocortin receptor, in a manner sufficient to reduce the inflammatory cytokine cascade.

In other embodiments, the invention is directed to methods of reducing levels of an inflammatory cytokine in a mammal. The methods comprise administering to the mammal any of the above peptides that activate a mammalian melanocortin receptor, in a manner sufficient to reduce levels of the inflammatory cytokine.

Additionally, the invention is directed to methods of treating an overweight mammal. The methods comprise administering to the mammal any of the above peptides that activate a mammalian melanocortin receptor.

In further embodiments, the invention is directed to methods of decreasing food intake in a mammal. The methods comprise administering to the mammal any of the above peptides that activate a mammalian melanocortin receptor, in a manner sufficient to decrease food intake in the mammal.

The invention is also directed to methods of inhibiting innate immunity in the digestive system of a mammal. The methods comprise administering to the mammal any of the above peptides that activate a mammalian melanocortin receptor, in a manner sufficient to inhibit innate immunity in the mammal.

BRIEF DESCRIPTION OF THE DRAWINGS

FIG. 1 shows relevant sequence analysis. Panel A shows sequences of all four of the common melanocortins of mammals that are derived from one pro-opiomelanocortin (POMC) Precursor, gamma-MSH, beta-MSH, alpha_MSH and ACTH (SEQ ID Nos: 19-22, respectively) in comparison to MECO-1 (1-33) (SEQ ID No: 1). Panel B shows the C-termini of the two elongation factors of human mitochondria, EFG1 and EFG2 (SEQ ID Nos: 3 and 4, Respectively) compared to MECO-1 (SEQ ID No:1). Note that each of them is about as close to MECO-1 as to each other. Panel C shows the several sequence matches (From top to bottom: SEQ ID Nos: 15, 5-13, 16 and 17, respectively) with MECO-1 (SEQ ID No:1)using BLAST analysis.

DETAILED DESCRIPTION OF THE INVENTION

Figure 2A:
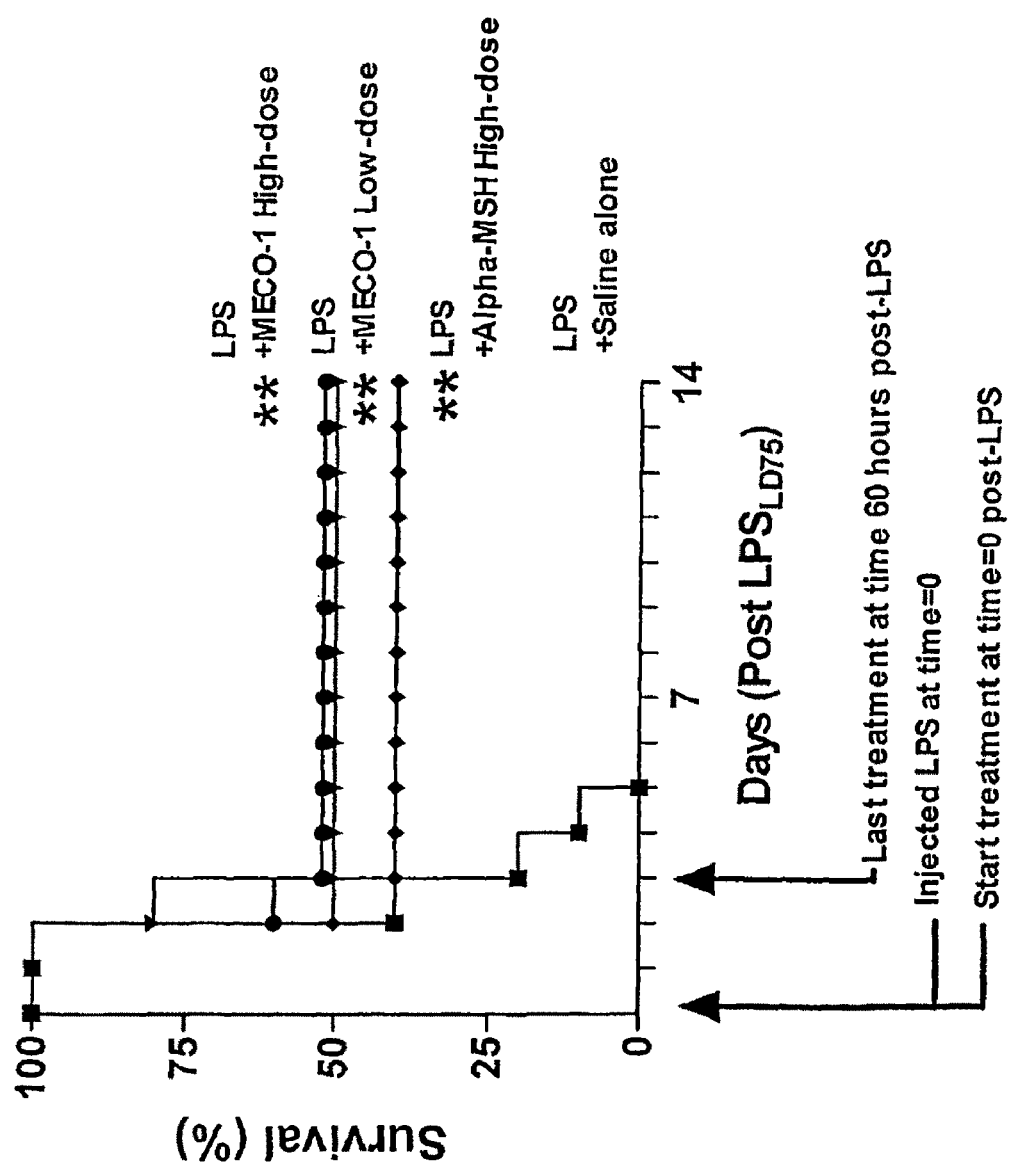
FIG. 2 is graphs demonstrating the ability of MECO-1 to rescue LPS-challenged mice and mice having lethal sepsis. Panel A. Balb/c mice were injected once intraperitoneally with LPS at a dose estimated to be an LD75. Immediately thereafter, the first doses of MECO-1 at 0.5 mg/kg (low dose, n=10), MECO-1 at 5 mg/kg (high dose, n=10), α-MSH at 5 mg/kg (high dose, n=10) or saline alone (n=10) were administered intraperitoneally. Peptide or saline were given twice daily for three days for a total of six doses. Survival was monitored daily for two weeks. The survival benefit of MECO-1 and α-MSH were each statistically significant (p<0.01-log-rank test) versus-saline treated mice. Panel B. Balb/c mice were subjected to cecal ligation and puncture (CLP). Starting 24 hours post-surgery, treatment was inaugurated, 2 doses daily for three days, a total of six doses; MECO-1 at 0.5 mg/kg (low dose, n=10) and MECO-1 at 5 mg/kg (high dose, n=10) were compared to saline alone (n=13) and α-MSH at 5 mg/kg (high dose, n=10). Animals were monitored for survival for 14 days. The survival benefit of MECO-1 was statistically significant (high dose p<0.01 and low dose *p<0.05-log-rank test). In this study, one α-MSH animal died on the last day of the experiment, so that the benefit of α-MSH escaped significance (p=0.08 changed from p<0.05). Note that the high dose of MECO-1 is equal in mg/kg to the high dose α-MSH but is less than half on a molar basis. Low dose MECO-1 is ten-fold less than the high dose of MECO-1 and less than one-twentieth on a molar basis of the high dose of α-MSH. The data with CLP (and with LPS) suggest the possibility that in protecting mice from death, MECO-1 may be up to thirty times more potent than α-MSH, whereas in vitro they appear to be equipotent.

The inventors have identified peptides that mimic melanocyte stimulating hormones by activating mammalian melanocortin receptors, and inhibit release of proinflammatory cytokines. The peptides are effective treatments for inhibiting the release of inflammatory cytokines and diseases characterized by excessive release of inflammatory cytokines. See Example.

Abbreviations: ACTH, adrenocorticotropic hormone; MSH, melanocyte stimulating hormone; CLP, cecal ligation and puncture; EF-G, elongation factor-G; HMGB1, high mobility group box 1 protein; LPS, lipopolysaccharide; MC1R, melanocortin-1 receptor (same notation for MC2R-MC5R); MECO-1, melanocortin-*E. coli*-1; POMC, pro-opiomelanocortin; TNF, tumor necrosis factor.

As established in the examples below, the peptide MECO-1 (SEQ ID NO:1) attenuates release of inflammatory cytokines and protects against sepsis, apparently attributable to its activation of MC1R and possibly other receptors targeted by mammalian melanocortins. In this way, MECO-1 mimics α-melanocyte stimulating hormone (α-MSH). MECO-1 is the C-terminal 33 amino acids of *E. coli* elongation factor-G, and is released by *E. coli*. Without being bound by any particular mechanism or physiological role, it is believed that MECO-1 and similar peptides inhibit mammalian innate immune systems from reacting to resident gut bacteria (and other inflammatory stimuli) by releasing inflammatory cytokines.

The examples also establish that MECO-1 suppresses food intake, apparently attributable to its activation of MC4R.

Figure 1:
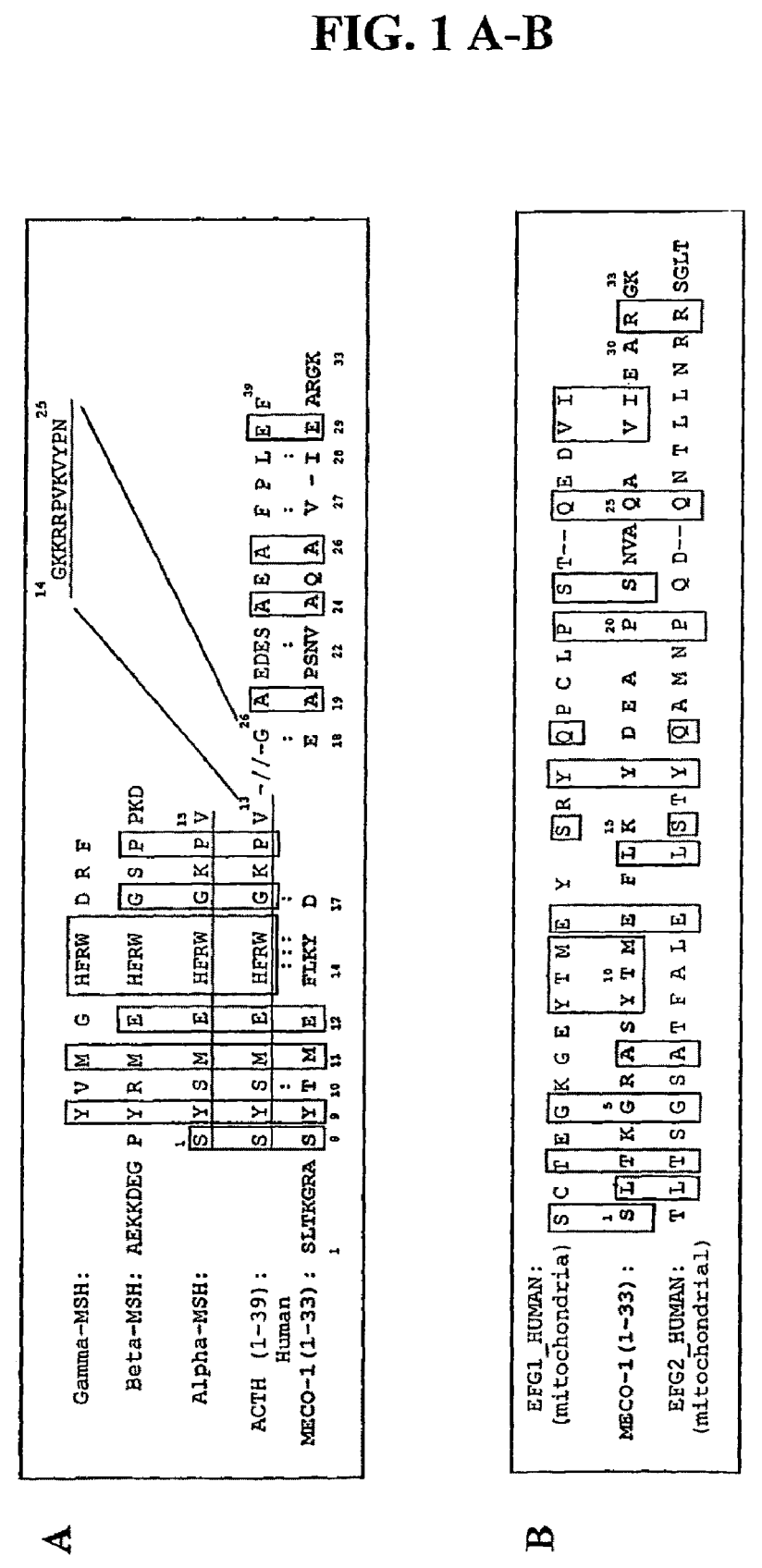

The four mammalian melanocortins, adrenocorticotropic hormone (ACTH) and α,β-, and γ-melanocyte stimulating hormones (MSH) are encoded in the pro-opiomelanocortin (POMC) gene (FIG. 1) (Cone, 2000; Lerner, 1993; Eberle, 2000; Hruby and Han, 2000; Mains et al., 1977; Roberts and Herbert, 1977; Kita et al., 1979). These peptides activate the adenylate cyclase pathway through five distinct G-protein linked (seven transmembrane) melanocortin receptors (MC1R through MC5R). Biologically relevant endpoints include stimulation of adrenal steroid synthesis (via ACTH action on MC2R) and skin darkening (largely via α-MSH action on MC1R) as well as inhibition of inflammation (mostly α-MSH action via MC1R on macrophages and other immune cells) and suppression of food intake (mostly via α-MSH action on MC4R on hypothalamic neurons) (Cone, 2000; Taunton et al., 1967; Lefkowitz et al., 1070; Schimmer et al., 1968; Gerst et al., 1988; Mountjoy et al., 1992; Saez et al., 1978; Chhajlani and Wikberg, 1996; Haynes et al., 1960). The very rare patients with genetic defects in the pro-opiomelanocortin gene manifest early onset obesity, adrenal insufficiency and red hair. The gene for the melanocortin-4 receptor (MC4R) is the most common site of single gene defects in obesity, having been detected in 5% of severely obese humans where it is characterized by onset at a young age and binge eating (Farooqi and O'Rahilly, 2005; Damcott et al., 2003; Krude et al., 1998; Yeo et al., 1998; Vaisse et al., 1998).

The inventors have also determined that the analogous region of elongation factor-G1 (EF-G1) and elongation factor-G2 (EF-G2) from humans, having SEQ ID NO:3 and 4, respectively, as well as from *Bacterioides fragilis* and *Bacterioides thetaiotamicron* (SEQ ID NO:16 and 17, respectively) also has the above-described MSH activity (see Examples). Based on these findings, the skilled artisan would expect that any peptides comprising the C-terminal 33 amino acids of any elongation factor-G would have the above-described MSH activity.

Thus, in some embodiments, the invention is directed to isolated and purified peptides of less than 680 amino acids or mimetics. The peptides comprise 33 amino acids or mimetics of a naturally occurring prokaryotic or mitocliondrial elongation factor-G corresponding to amino acids 671-703 of elongation factor-G (EF-G) of *E. coli*, having SEQ ID NO:14. In preferred embodiments, the peptide activates a mammalian melanocortin receptor. In more preferred embodiments, the melanocortin receptor is a melanocortin-4 receptor, a melanocortin-3 receptor or a melanocortin-1 receptor. Any particular peptide of these embodiments can be tested for the ability to activate melanocortin receptors without undue experimentation, for example by using the in vivo cecal ligation and puncture (CLP) test, or added melanocortin receptor antibody or melanocortin receptor antagonist, such as agouti or agouti-related peptide. Both of these tests are further elaborated in examples below.

As used herein, a mimetic or peptidomimetic is a compound that is capable of mimicking a natural parent amino acid in a protein, in that the peptidomimetic does not affect the activity of the protein. Proteins comprising peptidomimetics are generally not substrates of proteases and are likely to be active in vivo for a longer period of time as compared to the natural proteins. In addition, they could be less antigenic and show an overall higher bioavailability. The skilled artisan would understand that design and synthesis of peptidomimetics that could substitute for amino acids of any particular peptide (such as the peptides of this invention) would not require undue experimentation. See, e.g., Ripka et al., 1998; Kieber-Emmons et al., 1997; Sanderson, 1999.

The peptide can comprise the 33-mer along with any other moiety, for example additional amino acids or mimetics corresponding to the EF-G from which the 33-mer was derived or another EF-G; another protein or peptide, such as an antibody binding site (e.g., in order to target the peptide to a particular organ or cell type), another functional peptide (e.g., a cytokine or a protein that activates a particular receptor, to give the peptide bifunctional activity), or a His-6 moiety (to facilitate purification of the peptide); a radioactive or fluorescent moiety (to facilitate detection and/or quantification of the peptide); PEG moieties (to provide extended release characteristics); or a small molecule such as a drug.

In preferred embodiments, the peptide is less than 100 amino acids or mimetics. In more preferred embodiments, the peptide consists of 33 amino acids or mimetics, for example SEQ ID NO:1.

The peptide can also comprise any 33-mer corresponding to amino acids 671-703 of elongation factor-G (EF-G) of *E. coli* having SEQ ID NO:14. Examples include SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16 and SEQ ID NO:17. Any such peptide would be expected to have the above-described MSH activity. Preferably, the peptide comprises SEQ ID NO:1.

As discussed above, the invention peptide preferably consists only of the relevant 33-mer, e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17. In the most preferred embodiments, the peptide consists of SEQ ID NO:1.

As discussed above, since the 33-mer having the sequence of the *E. coli*, the *B. fragilis*, and the *B. thetaiotamicron* C-terminus of EF-G (i.e., MECO-1 = SEQ ID NO:1), as well as the corresponding sequence of the human EF-G1 and EF-G2, have the above-described MSH activity, the skilled artisan would expect corresponding EF-G C-terminal sequences from other organisms (including any prokaryotes or eukaryotes) would have the same activity. Such bacterial sequences that are similar to MECO-1 are provided as SEQ ID NO:5-13 and 15-17. Based on this analysis, the skilled artisan would expect any peptide encompassed by SEQ ID NO:2 would have the above-described MSH activity. In the description of SEQ ID NO:2 in the Appendix below, a moiety separated by a slash provides alternative amino acids or mimetics for that moiety. For example, since the second moiety in SEQ ID NO:2 is described in the Appendix as (L/Q/S), that moiety can be leucine ("L"), glutamine ("Q") or serine ("S"). This represents the alternative possibilities at the second moiety from the C-terminal corresponding sequences of EF-Gs provided in FIG. 1.

Thus, in other embodiments, the invention is directed to isolated and purified peptides of less than 680 amino acids or mimetics. The peptides comprise 33 amino acids or mimetics having SEQ ID NO:2. In preferred embodiments, the peptide activates a mammalian melanocortin receptor. In more preferred embodiments, the melanocortin receptor is a melanocortin-4 receptor, a melanocortin-3 receptor or a melanocortin-1 receptor. As with the embodiments described above, any particular peptide of these embodiments can be tested for the ability to activate melanocortin receptors without undue experimentation.

In other preferred embodiments, the peptide consists of less than 100 amino acids or mimetics; more preferably the peptide consists of 33 amino acids or mimetics.

In these embodiments, the peptide preferably comprises SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17. In more preferred embodiments, the peptide comprises SEQ ID NO:1. Since the peptide preferably consists of 33 amino acids or mimetics, the peptide more preferably consists of SEQ ID NO:1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17; most preferably SEQ ID NO:1.

The peptides described above can be usefully produced genetically, using a vector encoding the peptide. Thus, the present invention is additionally directed to vectors encoding the above peptides. In some embodiments, the vector is capable of infecting a prokaryote, in order to easily produce the peptide in bacterial culture. A prokaryote comprising such a vector can also be used to inoculate a mammal, where the production of the transgenic peptide in the mammalian gut could be therapeutic (see discussion of methods of treatment below).

The above-described vectors can also be usefully prepared, without undue experimentation, to be capable of infecting a mammalian cell. Such vectors can be used to directly infect a mammalian cell, when the mammalian cell would then produce the transgenic peptide. In preferred embodiments, those vectors are viral vectors.

In further embodiments, the invention is directed to transgenic cells comprising the above vectors. As indicated above, such transgenic cells can be a prokaryote. Preferably, the prokaryote is adapted to reside in a mammalian gut. Most preferably, the prokaryote is an *E. coli*. The transgenic cell can also be a mammalian cell.

The invention is also directed to methods of reducing or preventing release of an inflammatory cytokine from a mammalian cell. The methods comprise contacting the cell with any of the above peptides that activate a mammalian melanocortin receptor (preferably a melanocortin-1 receptor) in a manner sufficient to reduce or prevent release of the inflammatory cytokine. Non-limiting examples of such inflammatory cytokines are tumor necrosis factor-α (TNF-α), interleukin (IL)-1β, IL-6, IL-18 and HMGB1. In preferred embodiments, the inflammatory cytokine is TNF-α, IL-6 or HMGB-1, since the presence of those three cytokines were specifically shown in the Example below to be reduced in vitro and in vivo following treatment with MECO-1. Based on that result, however, it is expected that other inflammatory cytokines, e.g., IL-1β and IL-18, would be reduced by treatment with the peptides of the present invention.

In preferred embodiments, the cell is a macrophage, since macrophages are major producers of mammalian inflammatory cytokines. Central nervous system (CNS) administration would also be expected to suppress peripheral inflammation.

In these embodiments, the cell can be treated directly with the peptide, for example by contacting the cell with a solution of the peptide in vitro, or by administering the peptide to a mammal having the cell. Alternatively, the cell can be treated, either in vitro, or in vivo (e.g., to a mammal having the cell) with the above-described vector that is capable of infecting the cell. The cells of these embodiments that are treated in vitro can be further transplanted into a live mammal in an ex vivo protocol. The cells can also be treated by the peptide produced naturally or transgenically by another mammalian cell or by a prokaryotic cell, where the peptide diffuses, or is circulated or otherwise transported, to the treated cell.

As indicated above, the cell of these methods can be in a live mammal, to which the peptide is administered. In these embodiments, it is preferred that the peptide is in a pharmaceutical composition.

The above-described compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, enteric, lingual, sublingual, intrarectal, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

In some aspects of these embodiments where the cell is in a living mammal, the mammal has a condition mediated by an inflammatory cytokine cascade. Nonlimiting examples of such conditions include appendicitis, peptic, gastric or duodenal ulcers, peritonitis, pancreatitis, ulcerative, pseudomembranous, acute or ischemic colitis, ileus, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alveolitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Type II diabetes, ankylosing spondylitis, Berger's disease, Retier's syndrome, and Hodgkins disease. In some preferred embodiments, the condition is appendicitis, peptic, gastric or duodenal ulcers, peritonitis, pancreatitis, ulcerative, pseudomembranous, acute and ischemic colitis, hepatitis, Crohn's disease, asthma, allergy, anaplylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is sepsis, septicemia, or endotoxic shock, or peptic, gastric or duodenal ulcers, ulcerative, pseudomembranous, acute or ischemic colitis, ileus, diverticulitis, epiglottitis, achalasia, cholangitis, cholecystitis, Crolin's disease, enteritis or Whipple's disease.

These methods are useful for any mammal, including experimental animals such as rats, mice and guinea pigs; domestic animals such as horses, pigs, cows and sheep; companion animals such as dogs, cats, hamsters and ferrets; captive animals such as zoo animals, and humans. Preferably, the mammal is a human.

In related embodiments, the invention is directed to methods for treating a mammal suffering from a condition mediated by an inflammatory cytokine cascade. The methods comprise administering to the mammal any of the above peptides that activate a mammalian melanocortin receptor (preferably a melanocortin-1 receptor), in a manner sufficient to reduce the inflammatory cytokine cascade.

As with the relevant methods described above, the peptide can be administered to the mammal as a pharmaceutical composition. Alternatively, the peptide is administered to the mammal by administration of a prokaryote expressing the peptide from a transgene or a naturally occurring prokaryote selected to express a sufficient amount of the peptide, or by administering a vector capable of infecting cells of the mammal and expressing the peptide. Administration of the prokaryotes can be, e.g., as a pill or in a food. Such prokaryotes can provide a probiotic effect by establishing themselves in the gut microflora, where they continually produce the peptide.

In preferred embodiments, levels of at least one of the inflammatory cytokines TNF-α, IL-1β, IL-6, IL-18 or HMGB1 are reduced in the mammal. More preferably, levels of TNF-α, IL-6, or HMGB1 levels are reduced in the mammal.

In some aspects of these embodiments, the condition is appendicitis, peptic, gastric or duodenal ulcers, peritonitis, pancreatitis, ulcerative, pseudomembranous, acute or ischemic colitis, ileus, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alveolitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndromes Behcets's syndrome, allograft rejection, graft-versus-host disease, Type I diabetes, ankylosing spondylitis, Type II diabetes, ankylosing spondylitis, Berger's disease, Retier's syndrome, and Hodgkins disease.

Preferably, the condition is appendicitis, peptic, gastric or duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease; most preferably, the condition is sepsis, septicemia, or endotoxic shock, or peptic, gastric or duodenal ulcers, ulcerative, pseudomembranous, acute or ischemic colitis, ileus, diverticulitis, epiglottitis, achalasia, cholangitis, cholecystitis, Crohn's disease, enteritis or Whipple's disease.

In other preferred embodiments, the mammal is a human.

The invention is further directed to methods for treating a mammal at risk for a condition mediated by an inflammatory cytokine cascade. The methods comprise administering to the mammal any of the above peptides that activate a mammalian melanocortin receptor (preferably a melanocortin-1 receptor), in a manner sufficient to reduce the inflammatory cytokine cascade.

In preferred embodiments, levels of at least one of the inflammatory cytokines TNF-α, IL-1β, IL-6, IL-18 or HMGB1 are reduced in the mammal. More preferably, levels of TNF-α, IL-6, or HMGB1 levels are reduced in the mammal.

In some aspects of these embodiments, the condition is appendicitis, peptic, gastric or duodenal ulcers, peritonitis, pancreatitis, ulcerative, pseudomembranous, acute or ischemic colitis, ileus, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alveolitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, Warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Type II diabetes, ankylosing spondylitis, Berger's disease, Retier's syndrome, and Hodgkins disease.

Preferably, the condition is appendicitis, peptic, gastric or duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease; most preferably, the condition is sepsis, septicemia, or endotoxic shock, or peptic, gastric or duodenal ulcers, ulcerative, pseudomembranous, acute or ischemic colitis, ileus, diverticulitis, epiglottitis, achalasia, cholangitis, cholecystitis, Crohn's disease, enteritis or Whipple's disease.

In other preferred embodiments, the mammal is a human.

In other embodiments, the invention is directed to methods of reducing levels of an inflammatory cytokine in a mammal. The methods comprise administering to the mammal any of the above peptides that activate a mammalian melanocortin receptor (preferably a melanocortin-1 receptor), in a manner sufficient to reduce levels of the inflammatory cytokine.

In some aspects of these embodiments, the inflammatory cytokine is TNF-α, IL-1β, IL-6, IL-18 or HMGB1. Preferably, the inflammatory cytokine is TNF-α, IL-6, or HMGB1.

With these methods, the mammal is preferably suffering from, or at risk for, a condition mediated by an inflammatory cytokine cascade. Nonlimiting examples of such conditions include appendicitis, peptic, gastric or duodenal ulcers, peritonitis, pancreatitis, ulcerative, pseudomembranous, acute or ischemic colitis, ileus, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alveolitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Type H diabetes, ankylosing spondylitis, Berger's disease, Retier's syndrome, and Hodgkins disease.

In some preferred embodiments, the condition is appendicitis, peptic, gastric or duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is sepsis, septicemia, or endotoxic shock, or peptic, gastric or duodenal ulcers, ulcerative, pseudomembranous, acute or ischemic colitis, ileus, diverticulitis, epiglottitis, achalasia, cholangitis, cholecystitis, Crohn's disease, enteritis or Whipple's disease.

In other preferred embodiments, the mammal is a human.

As discussed above, individuals that have low activation of melanocortin-4 receptors are overweight and binge, presumably because their food intake suppression mechanisms are defective. It is expected, therefore, that treatment of such individuals with the peptides of the present invention would be an effective treatment of overweight mammals. The food intake suppression effects of MECO-1 are confirmed in Example 3.

Thus, the invention is additionally directed to methods of treating an overweight mammal. The methods comprise administering to the mammal any of the above-described peptides that activate a mammalian melanocortin receptor, preferably a melanocortin-4 receptor. Preferably, the peptide administration causes weight reduction in the mammal. In other preferred embodiments, the mammal is a human, although it is expected to be effective in any mammals.

In additional preferred embodiments of these methods, the mammal has a melanocortin deficiency, preferably due to a pro-opinomelanocortin gene defect.

As with the relevant methods described above, the peptide can be administered to the mammal as a pharmaceutical composition. Alternatively, the peptide is administered to the mammal by administration of a prokaryote expressing the peptide from a transgene or a naturally occurring prokaryote selected to express a sufficient amount of the peptide, or by administering a vector capable of infecting cells of the mammal and expressing the peptide. Administration of the prokaryotes can be, e.g., as a pill or in a food. Such prokaryotes can provide a probiotic effect by establishing themselves in the gut microflora, where they continually produce the peptide.

In further embodiments, the invention is directed to methods of decreasing appetite, decreasing food intake, decreasing body weight, and/or decreasing energy conservation in a mammal. The methods comprise administering to the mammal any of the above peptides that activate a mammalian melanocortin receptor, preferably a melanocortin-4 receptor, in a manner sufficient to decrease appetite, decrease food intake, decrease body weight, and/or decrease energy conservation in the mammal.

In some embodiments, the mammal is overweight. In preferred embodiments, the mammal is a human, although it is expected to be effective in any mammals.

As with the relevant methods described above, the peptide can be administered to the mammal as a pharmaceutical composition. Alternatively, the peptide is administered to the mammal by administration of a naturally occurring prokaryote or a prokaryote expressing the peptide from a transgene (as a probiotic), or by administering a vector capable of infecting cells of the mammal and expressing the peptide.

The invention is also directed to methods of inhibiting innate immunity in the digestive system of a mammal. The methods comprise administering to the mammal any of the above peptides that activate a mammalian melanocortin receptor (preferably a melanocortin-1 receptor), in a manner sufficient to inhibit innate immunity in the mammal.

In preferred embodiments, the mammal is a human, although it is expected to be effective in any mammals.

As with the relevant methods described above, the peptide can be administered to the mammal as a pharmaceutical composition. Alternatively, the peptide is administered to the mammal by administration of a prokaryote expressing the peptide from a transgene, or by administering a vector capable of infecting cells of the mammal and expressing the peptide.

Since the peptides of the present invention are expected to activate all melanocortin receptors, the peptides would be expected to darken skin by activating the melanocortin-4 receptor. Thus, the present invention is additionally directed to methods of darkening skin of a mammal. The methods comprise administering to the skin any of the above peptides that activate a mammalian melanocortin receptor, in a manner sufficient to darken the skin.

Preferably, the mammal is a human.

The present invention also provides in vitro and in vivo assays for evaluating the melanocortin receptor-stimulating ability of the above peptides. The in vivo assays involve the cecal ligation and puncture (CLP) procedure in Example; the in vitro assays involve the ability of the peptide to inhibit inflammatory cytokine release from a cell in the presence or absence of an inhibitor or a melanocortin receptor (see Example).

Thus, the invention is also directed to methods of evaluating the melanocortin receptor-stimulating ability of any of the above-described peptides. The methods comprise determining the ability of the peptide to inhibit sepsis in an animal that has undergone cecal ligation and puncture. The inhibition of sepsis can be determined by any means known in the art, including but not limited to determining inhibition of death of the animals, and determination of inhibition of release of inflammatory cytokines from cells in the animal.

In further embodiments, the invention is directed to additional methods of evaluating the melanocortin receptor-stimulating ability of any of the above-described peptides. The methods comprise determining the ability of the peptide to inhibit release of an inflammatory cytokine from a cell in the presence or absence of an inhibitor of a melanocortin receptor.

The cells of these embodiments must have the ability to produce inflammatory cytokines (e.g., macrophages or macrophage-like cells—see Example), and must also usually be stimulated to produce inflammatory cytokines, e.g., by LPS treatment. Thus, in preferred embodiments, the cell is treated with LPS.

Any inhibitor of melanocortin receptors can be used here. In some embodiments, the inhibitor of a melanocortin receptor is agouti.

In some preferred embodiments of these methods, the melanocortin receptor-stimulating ability of the peptide is quantified relative to another melanocortin receptor-stimulating agent.

In additional embodiments, the invention is directed to methods of evaluating the melanocortin receptor-stimulating ability of a prokaryote producing any of the above-described peptides. The methods comprise administering the prokaryote enterically to a mammal, then determining the ability of the administered prokaryote to inhibit an effect of sepsis in an animal that has undergone cecal ligation and puncture.

Similarly, the invention is additionally directed to other methods of evaluating the melanocortin receptor-stimulating ability of a prokaryote producing any of the above-described peptides. The methods comprise combining the prokaryote with a cell capable of producing an inflammatory cytokine, then determining the ability of the prokaryote to inhibit release of an inflammatory cytokine from a cell in the presence or absence of an inhibitor of a melanocortin receptor. Similar to above described methods, the cell is preferably treated with LPS and the inhibitor is preferably agouti.

The above methods for evaluating the melanocortin receptor-stimulating ability of a prokaryote making the invention peptides can be used with naturally occurring prokaryotes (e.g., those that can be added to foods as a probiotic), or with prokaryotes that transgenically produces the peptide.

The present invention is also directed to methods of increasing food intake in a mammal. The methods comprise suppressing MECO-1 activity in the mammal. These These methods are not limited to any particular method of suppressing-MECO-1 activity in the mammal. MECO-1 activity is suppressed by administering a MECO-1 antagonist to the mammal. Included here are antibodies or aptamers that specifically bind to MECO-1. Peptides or small organic compounds that are MECO-1 antagonists can also be prepared by known methods. MECO-1 activity is suppressed by immunizing the mammal against MECO-1.

These methods are particularly useful for farm animals, to inhibit the food intake-suppressing ability of the MECO-1 and analogous compounds from the animal's gut microorganisms. These methods can also be used for humans with eating disorders or with diseases that cause wasting.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

A Peptide Released from *E. coli* is More Potent than α-MSH in Rescuing Septic Mice from Death Example Summary MECO-1 is a novel *E. coli* peptide, isolated from conditioned medium, whose structure corresponds to the 33 amino acid C-terminus of elongation factor-G (EF-G). When a synthetic replicate of MECO-1 was administered parenterally, it mimicked the human melanocortin α-MSH in rescuing mice from death due to cecal ligation and puncture (CLP), an experimental model of perforated appendix with peritonitis and sepsis. In these mice with CLP, administration of MECO-1 and α-MSH also blunted the rise in serum levels of tumor necrosis factor (TNF)-α, interleukin (IL)-6, and HMGB-1 (high mobility group box protein 1), three of the "inflammatory cytokine cascade" cytokines that contribute to the morbidity and mortality associated with sepsis and other inflammatory diseases or conditions. In vitro, the release of HMGB-1 from murine macrophage-like RAW 264.7 cells in response to LPS (lipopolysaccharide/endotoxin) was markedly blunted by MECO-1, α-MSH, and ACTH at 100 pM. Likewise, the multifold increase in TNF release generated by HMGB1 from RAW cells was substantially diminished by MECO-1, α-MSH, and ACTH at 1 pM. When freshly isolated human peripheral blood mononuclear cells were cultured in vitro and then exposed to HMGB1, the marked rise in TNF release was blunted by picomolar concentrations of MECO-1, α-MSH, and ACTH. The property of MECO-1 and of α-MSH to blunt the effect of HMGB1 on TNF release was abrogated by two agents that block the melanocortin-1 receptor (MC1R), (i) antibodies against that receptor and (ii) agouti, an endogenous peptide that blocks the effects of melanocortins on MC1R. It is hypothesized that MECO-1, released from *E. coli*, and other peptides like it from other bacteria in the colon, interacts continually with melanocortin-1 receptors (MC1R) on host cells to suppress inflammatory responses. This suppression of the host's innate immune system in its response to bacteria and to components of bacteria is probably necessary to allow the very large dense mass of microbes to co-exist harmoniously within the host. Disturbances in the balance between classical pro-inflammatory effects and the newly described anti-inflammatory effects of bacteria in the intestinal flora may play a role in diseases of humans.

Introduction

Shown here is that *Escherichia coli*, a classic component of the gut flora, releases a potent melanocortin-like peptide that at low picomolar concentrations can actively suppress components of the innate immune system in vitro, and is at least as potent as α-melanocyte stimulating hormone (MSH) in rescuing mice from lethal sepsis. This leads to the suggestion that the gut bacteria themselves may normally be producing hormone-like molecules that suppress the host's innate immune system by interacting with specific receptors for the host's endogenous hormones.

*E. coli* grown in totally synthetic medium rapidly release one or more melanocortin-related peptides into the medium. One of these, a 33 amino acid peptide (SEQ ID NO:1) that corresponds to the C-terminus of its elongation factor-G (EF-G), is characterized herein. This peptide, tested in the form of a synthetic replicate, interacts with a series of anti-ACTH antibodies and also robustly stimulates corticosterone release from rat adrenals (about as well as α-MSH). Established here is that this peptide, like α-MSH, interacts in vitro with MC1R on macrophages at low picomolar concentrations to inhibit the release of tumor necrosis factor (TNF)-α and interleukin-6 (IL-6), two cytokines released early in sepsis. It also inhibits production of HMGB1, a potent late-released cytokine that is linked to death from sepsis (Dumitriu et al., 2005; Lotze and Tracey, 2005; Yang et al., 2005; Wang et al., 2004; Wang et al., 1999; Li et al., 2004; Li et al., 2003).

The *E. coli*-derived peptide (designated "melanocortin-*E. coli*-1" or MECO-1, pronounced MEE-koe-wun) is at least as potent as α-MSH in rescuing mice from lethal sepsis induced by cecal ligation and puncture, an experimental model similar to perforated appendix with peritonitis in humans.

Materials and Methods

Materials. Recombinant rat HMGB1 was prepared as previously described (Wang et al., 1999), and passed over a polymyxin B column to remove any LPS contamination; the details of procedures used to free HMGB1 of LPS contamination have been covered elsewhere (Li et al., 2004). Final LPS content was determined using the *Limulus amebocyte* lysate (LAL) assay (BioWhittaker Inc, Walkersville, Md.) as described previously (Li et al., 2004; Li et al., 2003). LPS (LPS, *E. coli.* 0111:B4) and macrophage colony stimulating factor were purchased from Sigma Chemical (St. Louis, Mo.). Anti-MC1R antibody was purchased from Santa Cruz Biotechnology Inc. (Santa Cruz, Calif.). Mouse agouti (93-132)-NH2 was purchased from Phoenix Pharmaceuticals, Inc. (Belmont, Calif.). ACTH (1-39) and α-MSH was obtained from Bachem Bioscience Inc. (King of Prussia, Pa.).

Peptide synthesis. MECO-1 (33 amino acid peptide equivalent to C-terminus of elongation factor-G of *E. coli*) was synthesized and HPLC purified at 88.9% purity in Utah State University Biotechnology Center (Logan, Utah, USA). LPS was not detectable in the synthetic peptide preparations as measured by *Limulus amebocyte* lysate (LAL) assay (BioWhittaker Inc, Walkersville, Md.) as described above.

Amino acid sequence comparison of MECO-1. Using computer-assisted database, matching sequences were compared with MECO-1 by using the BLAST network service (http://ca.expasy.org/tools/blast, ExPASy BLAST2 Interface). The sequences of both peptides were aligned, and pairwise percentage similarities were calculated using the William Pearson's lalign program (using matrix file: BLOSUM 50, gap penalties: −14/4) (www.ch.embnet.org) (Thompson et al., 1994) (FIG. 1).

Animal experiments. In vivo studies were performed in accordance with National Institutes of Health guidelines and with the approval of the North Shore-Long Island Jewish Health System's Institutional Animal Care and Use Committee (IACUC). In mice, sepsis was induced by surgical ligation and perforation of the cecum, a widely used technique known as cecal ligation and puncture (CLP) (Wichmann et al., 1996). Briefly, male BALB/c mice (7-8 weeks old, 20-25 g) were anesthetized with a mixture of ketamine (100 mg/kg) and xylazine (8 mg/kg) intramuscularly, and a 15 mm midline incision was made to expose the cecum. After ligation of the cecum with a 6.0 silk suture below the junction of the ileocecal valve, the ligated cecal stump was perforated once with a 22-gauge needle. The cecum was then gently squeezed to extrude a small amount of feces through the perforation site. The cecum was restored to its normal intra-abdominal position, and the laparotomy was closed with 6.0 silk sutures. Immediately after CLP surgery, all animals were resuscitated with normal saline solution (subcutaneously 20 ml/kg body weight), and given a single dose of antibiotics (primaxin 0.5 mg/kg). In sham operated animals, the cecum was temporarily ligated, but the bowel was not be punctured; the animals did receive antibiotic treatment and resuscitative fluid. All animals were then returned to their cages with free access to food and water (Yang et al., 2004). At 24 hours after CLP, animals were randomly grouped, and received intraperitoneally MECO-1 (0.5 or 5 mg/kg), α-MSH, (5 mg/kg), or control vehicle (isotonic saline, 0.2 ml) at 24 hours post CLP. In protocol A, peptides (or vehicle) were administered twice daily on day 2, 3 and 4 post surgery. Survival was monitored twice daily for two weeks. In protocol B, a parallel experiment, peptides or vehicle were administered once at 24 hours. Survival was monitored twice daily after surgery. All animals were killed at 40 hours to measure blood levels of selected cytokines.

Cell cultures. Murine macrophage-like RAW 264.7 cells were obtained from ATCC (American Type Culture Collection, Manassas, Va.), and were grown in Dulbecco's Modified Eagle's Medium (DMEM, Life Technologies, Grand Island, N.Y.) containing 10% (vol/vol) heat-inactivated fetal bovine serum (FBS, Hyclone Lab. Inc., Logan, Utah), penicillin 100 U/ml, and streptomycin 100 mg/ml (BioWhittaker Inc, Walkersville, Md.). Cells were resuspended in medium and incubated in 24- or 48-well tissue-culture plates overnight in a humidified incubator (37° C., 5% $CO_2$). Growth medium was removed and replaced by Opti-MEM I serum-free medium (Life Technologies, Grand Island, N.Y.) overnight. In the experiments, cell monolayers were stimulated with HMGB1 or LPS, in the absence or presence of MECO-1 or α-MSH; cell-free supernatants were assayed for TNF by ELISA or HMGB1 by western blotting.

Human peripheral blood mononuclear cells were isolated by density gradient through Ficoll-Paque™ PLUS centrifugation (Amersham Pharmacia Biotech, Piscataway N.J.), and resuspended in RPMI 1640 containing 10% (vol/vol) heat-inactivated human serum (BioWhittaker Inc, Walkersville, Md.), penicillin 100 U/ml, and streptomycin 100 mg/ml, and incubated at 37° C. in a humidified incubator with 5% $CO_2$ atmosphere overnight. Nonadherent cells were discarded. Adherent monocytes were washed twice with PBS and were then resuspended in 12- and 24-well tissue culture plates and incubated in the same medium further enriched with 2.5 ng/ml macrophage colony-stimulating factor for 5-7 days (Rendon-Mitchell et al., 2003). The growth medium was removed and replaced by Opti-MEM I serum-free medium overnight. Cell monolayers were incubated with HMGB1, in the absence or presence of MECO-1 or α-MSH, and supernatants were assayed for TNF.

Western immunoblotting analysis. The levels of HMGB1 in the culture medium or murine serum were measured by western immunoblotting as previously described (Wang et al., 1999). Western blots were scanned with a silver image scanner (Silverscaner II, Lacie Limited, Beaverton, Oreg.), and the relative band intensity was quantified by using the NIH image 1.59 software. The levels of HMGB1 (expressed as % maximum effect) were calculated with reference to standard curves generated with purified rHMGB1 and expressed as mean±SEM of four experiments.

Cytokine assay. Concentrations of TNF and IL-6 were each determined using a commercially available enzyme-linked immunosorbent assay (ELISA) kit (R&D System Inc., Minneapolis, Minn.) as previously described (Rendon-Mitchell et al., 2003). The levels of TNF or IL-6 were calculated with reference to standard curves.

Statistical analysis. Kaplan-Meier analysis was used to determine statistical significance of the differences in survival of mice. $P \leq 0.05$ was considered significant.

Values in the figures were expressed as mean±SEM of two to three independent experiments where each experimental point was derived from duplicates or triplicates. Student's two-tailed t-test was used to compare the means between groups. A P-value of 0.05 or less was considered statistically significant.

Results

MECO-1 protects against LPS-induced lethality. Mice injected with a lethal dose of lipopolysaccharide endotoxin were rescued by the simultaneous administration of α-MSH or MECO-1, the melanocortin released from *E. coli* (FIG. 2A). In two experiments, none of the saline-treated mice survived (0 of 19), while MSH rescued 25% (5 of 20) and MECO-1 rescued 50% (15 of 30).

Figure 2B:
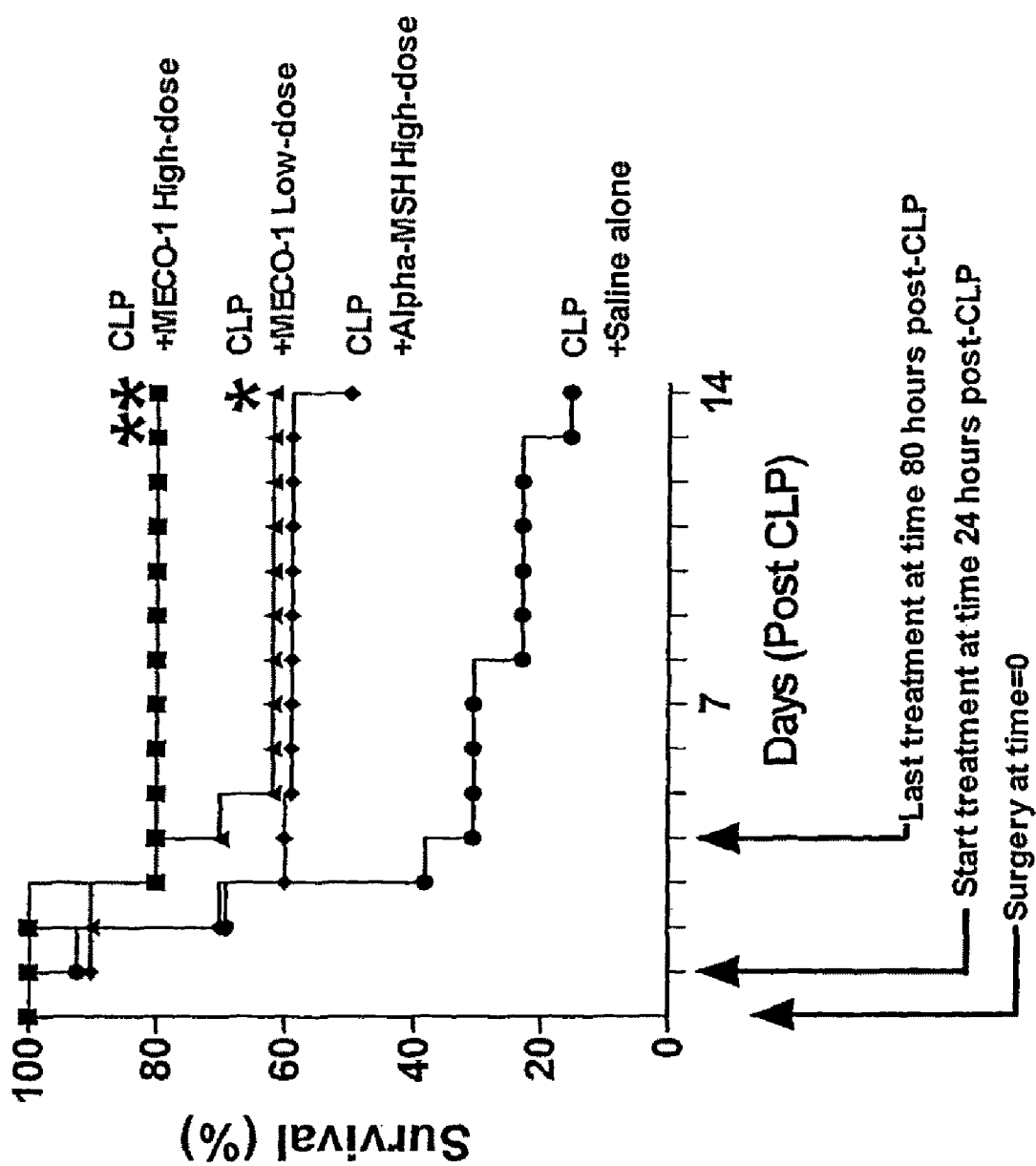

MECO-1 protects against CLP-induced lethality. With cecal ligation and puncture (CLP), a mouse model of sepsis similar to perforated appendix with peritonitis, only 50% of the mice were alive by day 3 and 15% by day 14 (FIG. 2B). α-MSH, as expected (Catania et al., 2004; Delgado et al., 1998), markedly improved survival to around 50% at day 14 (FIG. 2B). MECO-1 was at least as effective (FIG. 2B), so that at a comparable (or even smaller dose) 80% of the mice survived (p<0.01). Injections were started at 24 hours after surgery and continued through day 4 (administered twice daily for a total of six doses). In three experiments, 23% of the animals (9 of 39) with CLP survived. With α-MSH, 68% (15 of 22) survived, while with MECO-1, 66% (42 of 64) survived. Note that the high dose of MECO-1 is equal in mg/kg to the high dose α-MSH but is less than half on a molar basis. Low dose MECO-1 is ten-fold less than the high dose of MECO-1 and less than one twentieth on a molar basis of the high dose of α-MSH. This data indicates that, in protecting mice from death, MECO-1 appears to be thirty times more potent than α-MSH, whereas in vitro (see FIG. 4) they are approximately equipotent.

Figure 3:
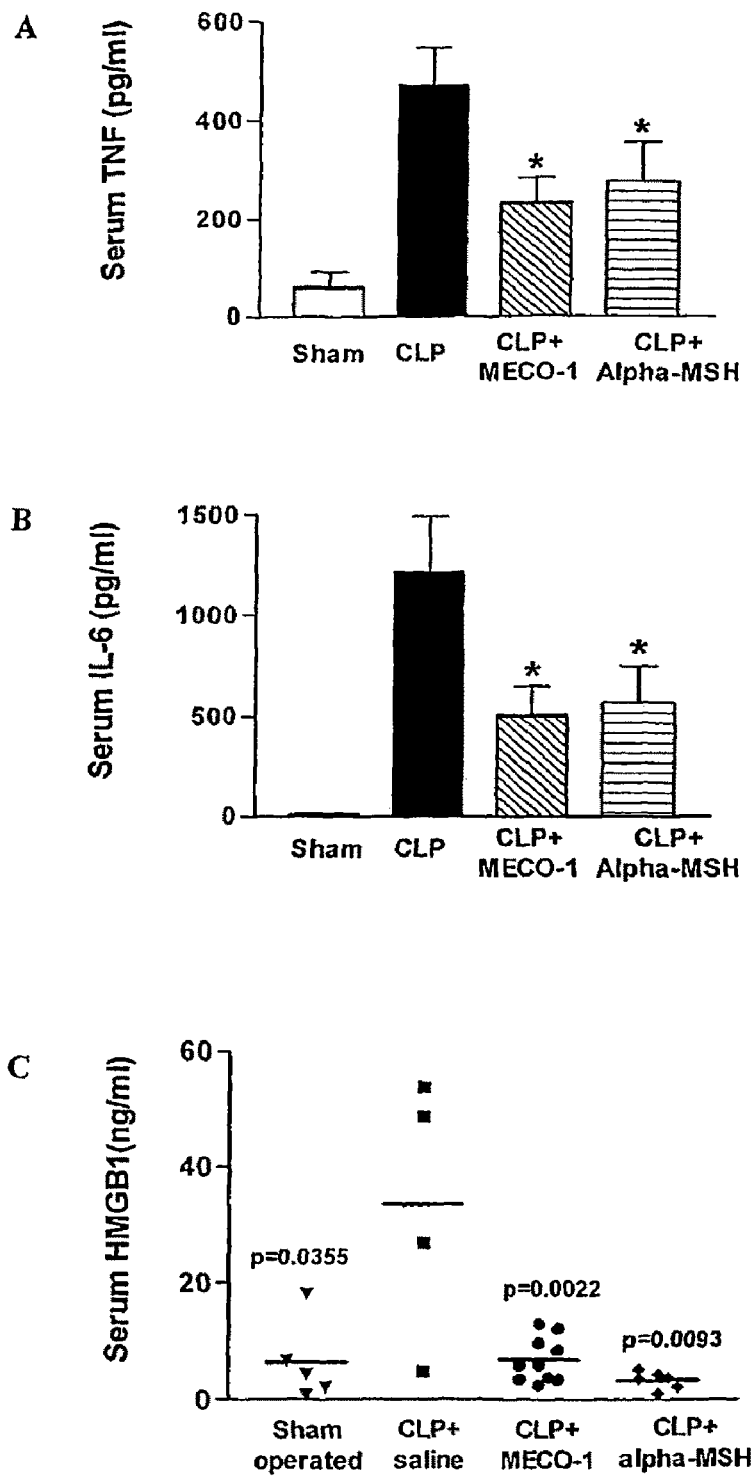
FIG. 3 is graphs of experimental results establishing that MECO-1 attenuates accumulation in blood of HMGB1 and other cytokines following cecal ligation. Balb/C mice underwent CLP as described in Materials and Methods. At 24 hours post-surgery the mice received one dose of saline (n=9), MECO-1 at 5 mg/kg (n=10), or α-MSH at 5 mg/kg (n=10) intraperitoneally. Survivors at 40 hours post-surgery were killed, and blood was obtained for measurement of cytokines. Serum levels of TNF and IL-6 were determined by ELISA, and expressed as mean±SEM of two independent experiments in duplicate (*p<0.05, vs. CLP alone). Serum HMGB1 levels were determined by Western blot analysis with reference to standard curves of purified HMGB1. Plotted are levels of HMGB1 in serum for each individual animal. Note that 5 (of the 9) treated with saline alone died before 40 hours and their results are not included. It is believed that some of the mice that perished before 40 hours may have had cytokine levels that were higher than those that survived and that differences reported here between CLP vs. CLP+melanocortin are less than might have been observed at an earlier time point.

MECO-1 attenuates the CLP-induced rise in serum cytokines. In a parallel experiment (designated protocol B in Methods), sham surgery or CLP was performed; one treatment (peptide or saline) was given at 24 hours; and at 40 hours, serum cytokines were measured (FIG. 3). Only 4 out of 9 of the CLP-operated saline-treated animals survived to 40 hours. The survivors had very high serum levels of TNF and IL-6, two cytokines characteristic of the early stages of sepsis. Six of ten α-MSH-treated animals and all ten of the MECO-1-treated animals survived to 40 hours. In the survivors at 40 hours, α-MSH- and MECO-1-treated animals showed significantly muted responses of TNF and of IL-6 (p<0.05). HMGB1, a major late cytokine, was elevated in 3 of 4 saline-treated CLP animals but in none of those treated with α-MSH or MECO-1 (FIG. 3).

Figure 4:
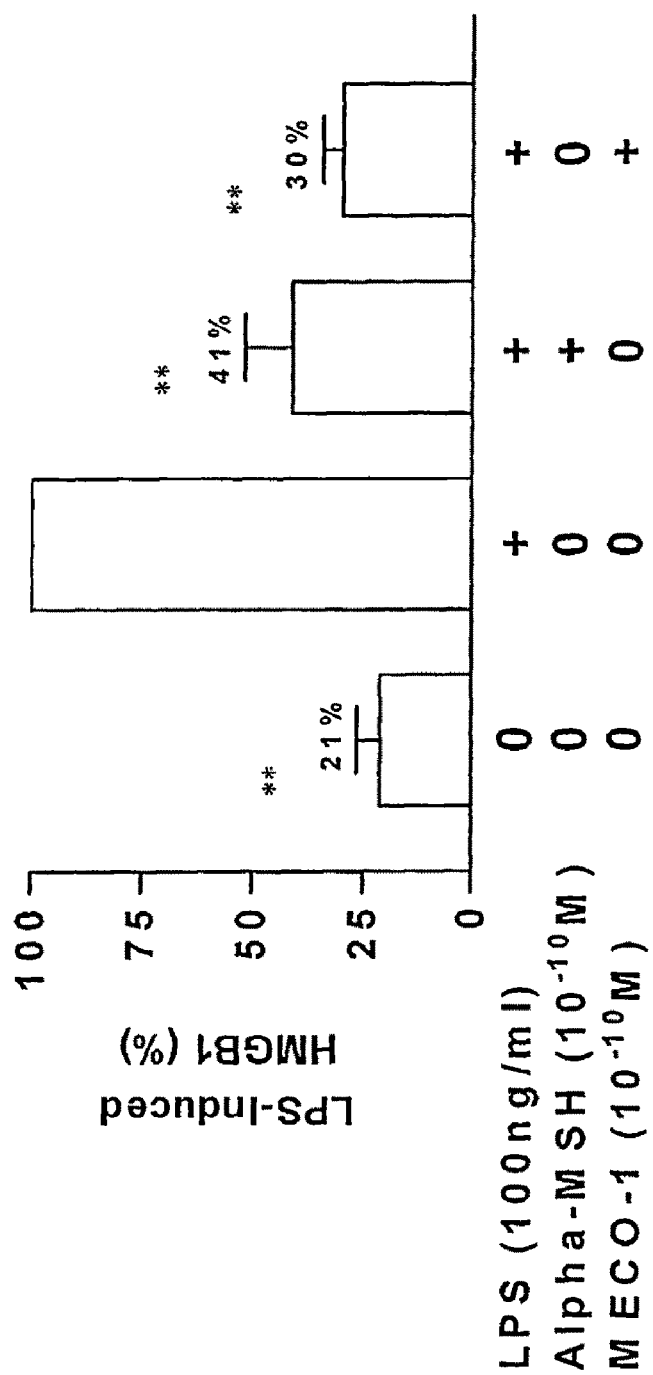
FIG. 4 is a graph of experimental results establishing that MECO-1 in vitro inhibited bacterial LPS-induced HMGB1 release. Murine macrophage-like RAW 264.7 cells were incubated with LPS (100 ng/ml) in the absence or presence of MECO-1 or α-MSH at 100 μM. At 16-20 hrs after stimulation, aliquots of cell-free medium were examined. HMGB1 levels in the (conditioned) culture medium were expressed as mean±SEM of four independent experiments with the peak level (obtained with LPS) set at 100%. The reductions in HMGB1 by MECO-1 and by α-MSH were significant (**P<0.01).

MECO-1 suppresses LPS-induced HMGB1 release by macrophages. In vitro cell systems were employed to explore further the effects of MECO-1 on pro-inflammatory cytokines. FIG. 4, a composite of four experiments, shows that LPS-induced release of HMGB1 by macrophage-like RAW cells after overnight incubation is significantly blunted by α-MSH and by MECO-1 at 100 pM (p<0.01). ACTH (1-39) at the same molar concentrations gave results indistinguishable from α-MSH.

Figure 5:
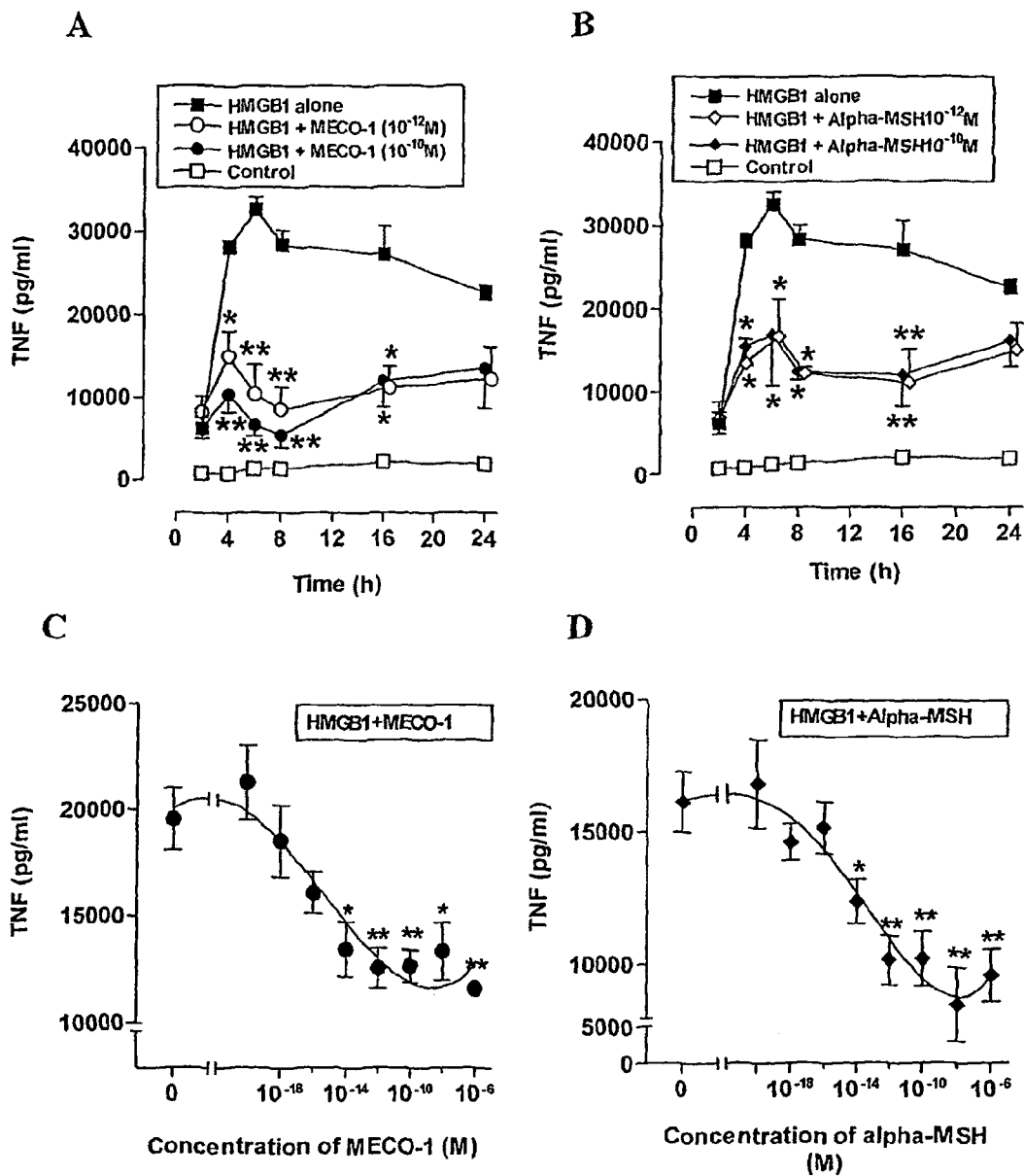
FIG. 5 is graphs of experimental results establishing that MECO-1 attenuates HMGB1-induced TNF release by macrophages in culture. Murine macrophage-like RAW 264.7 cells were incubated for up to 24 hours with purified recombinant HMGB1 (0.1 mg/ml) in the absence or presence of MECO-1 (Panel A), or α-MSH (Panel B), at $10^{-10}$ or $10^{-12}$ M. The levels of TNF in the culture medium were determined by ELISA and expressed as mean SEM of two independent experiments (in duplicate). *p<0.05, **p<0.01 vs. control ("HMGB1 alone"). In a third experiment, very similar results were obtained except that the maximum TNF release was observed at 16-24 h (not shown), similar to results of others (Gerst et al., 1988) with human endothelial cells. In Panels C and D, cells were incubated with HMGB1 for 6 hours with MECO-1 or a -MSH ($0-10^{-6}$ M). Data represent mean±SEM of three independent experiments performed in duplicate. At $10^{-14}$M peptide, results were significant at *p<0.05, and at $10^{-12}$M or more were typically **p<0.01.

MECO-1 suppresses HMGB1-induced TNF release. HMGB1 stimulates a rapid multifold increase in TNF release by RAW cells that is blunted substantially by 1 pM and 100 pM MECO-1 (FIG. 5A) and α-MSH (FIG. 5B). The blunting effect of the two peptides on HMGB1 release was observed over the period from 4-16 hours after addition of LPS (FIGS. 5A, B), with the largest difference detected at 6 hours. With a 6-hour incubation, both peptides showed dose dependence with significant effects noted with both at 10-14 M (FIGS. 5C, D). ACTH (1-39) gave very similar results (data not shown), with highly significant suppression in the subpicomolar range.

Figure 6:
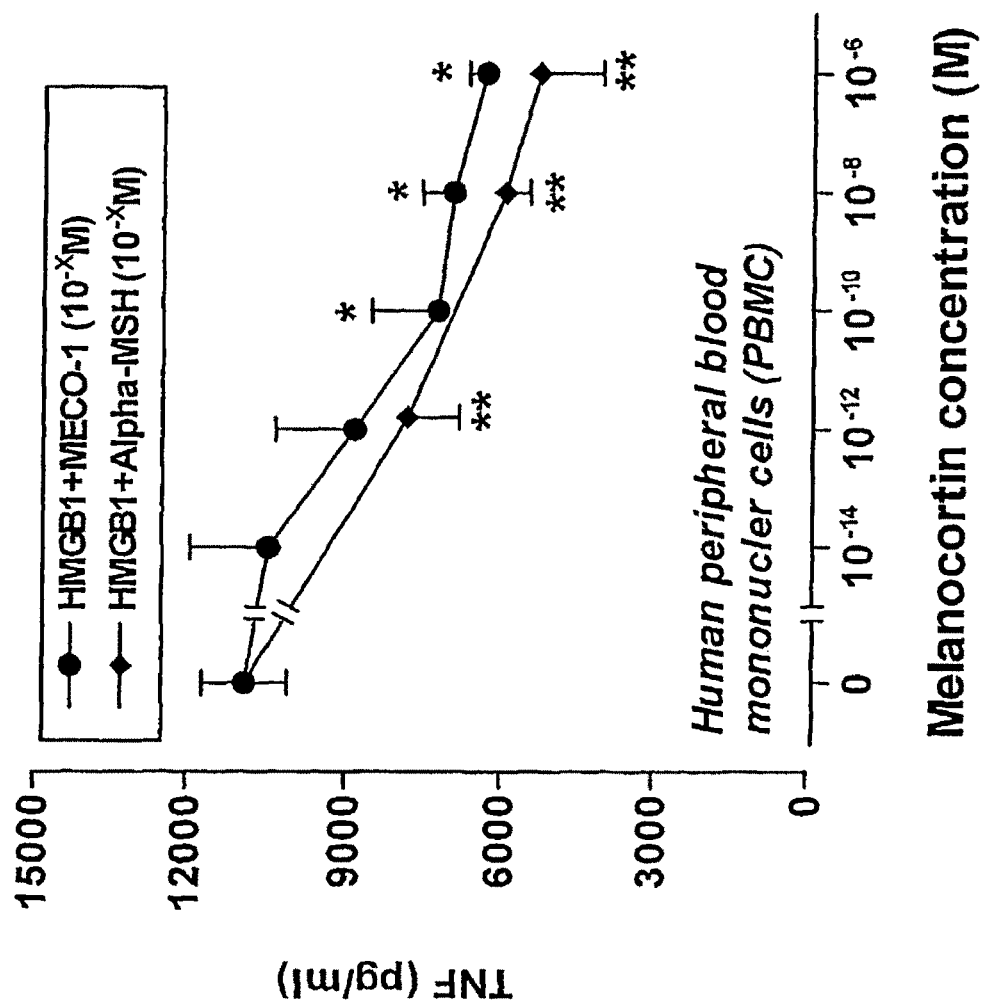
FIG. 6 is a graph of experimental data establishing that MECO-1 attenuates HMGB1-induced TNF release by human macrophages in culture. Human peripheral blood mononuclear cells (HuPBMC) were isolated by density gradient centrifugation through Ficoll-Paque™ PLUS, and cultured for 5-7 days in medium containing macrophage colony-stimulating factor (2.5 ng/ml) (Rendon-Mitchell et al., 2003). The differentiated human macrophages were subsequently incubated for 6 hours with HMGB1 (0.1 mg/ml) in the absence or presence of MECO-1 or α-MSH at indicated concentrations. The content of TNF in the cell-free medium was determined by ELISA, and expressed as mean±SEM of three independent experiments performed in duplicate. *p<0.05, **p<0.01 vs. control (=HMGB1 alone without added melanocortin peptide).

With human peripheral blood mononuclear cells (PBMC), α-MSH and MECO-1 caused very similar attenuation of HMGB1-induced TNF release, with significant effects in the picomolar range (FIG. 6). ACTH (1-39) gave very similar results (data not shown).

Figure 7:
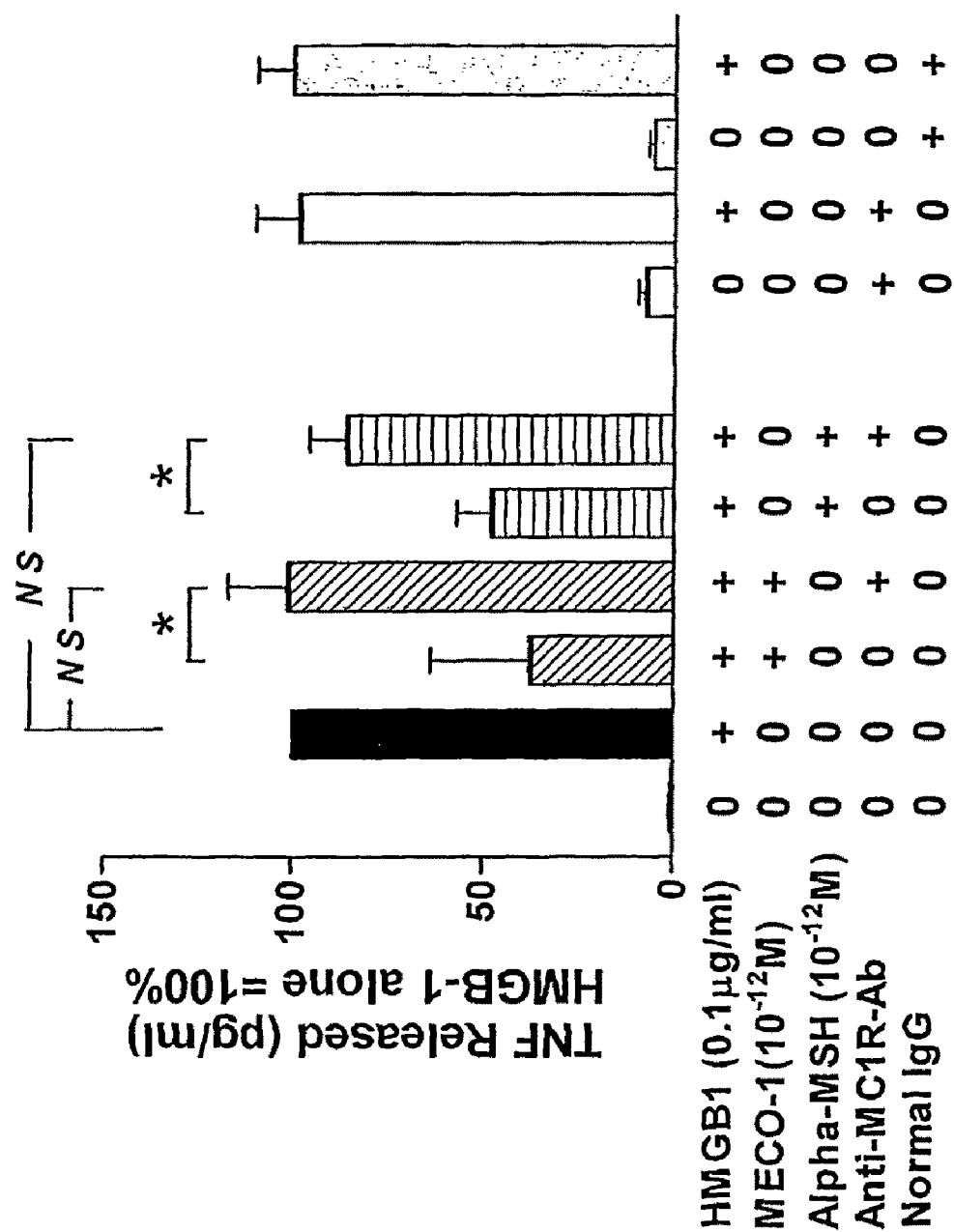
FIG. 7 is a graph of experimental results establishing that antibody to MC1R blocks the α-MSH and MECO-1 effect. Murine macrophage-like RAW 264.7 cells were pretreated with specific antibodies against α-MSH receptor-1 (MC1R) ("anti-MC1R Ab") for 10 minutes prior to addition of HMGB1 in the absence or presence of MECO-1 or α-MSH at $10^{-12}$M. At 6 h, the TNF content of the cell-free medium was determined by ELISA, and expressed as mean±SEM of two independent experiments performed in duplicate. Our results here differ from those of Taherzadeh et al. (1999), who found in a similar experiment that anti-MC1R increased the TNF release in response to LPS to a level higher than that observed with LPS alone. ACTH at the same concentration gave results that were indistinguishable from those of α-MSH and MECO-1.

MECO-1 and α-MSH effects are blocked by blockers of MC1R. Complete neutralization of the MECO-1 and α-MSH effects were obtained with an antibody directed against the melanocortin-1 receptor (MC1R) (FIG. 7). This is the receptor implicated as mediator of nearly all of α-MSH effects on macrophage/mononuclear cells as well as other direct (i.e. extra-adrenal) "anti-inflammatory" processes (Cone, 2000; Catania et al., 2004; Delgado et al., 1998). Note that with α-MSH and MECO-1, the anti-melanocortin-1 receptor antiserum restored TNF release to equal the level achieved with HMGB1 alone (in the absence of added α-MSH and MECO-1). By contrast Lipton et al. found that receptor antibody caused TNF release to exceed that induced by LPS alone; they proposed that the macrophages released endogenous α-MSH (Taherzadeh et al., 1999).

Agouti (Cone, 2000), the in vivo antagonist of α-MSH actions via MC1R, reversed the attenuation of LPS-induced TNF release by α-MSH and MECO-1. Note that agouti plus LPS raised TNF levels significantly above those observed with LPS alone (Table 1), which is consistent with recent observations that the MC1R receptor has a definite basal activity (Sanchez-Mas et al., 2004) that can be turned off by agouti, which acts as an inverses agonist to suppress the basal anti-inflammatory property of MC1R (Chai et al., 2003).

TABLE 1

Agouti inhibits the effects of MECO-1 and α-MSH on endotoxin-stimulated TNF release

| Agouti (pM) | MECO-1 ($10^{-12}$ M) | αMSH ($10^{-12}$ M) |
| --- | --- | --- |
| 0 | 52.9 ± 11.2 | 67.05 ± 10.2 |
| 10 | 134.3 ± 14.5** | 132.6 ± 4.9* |
| $10^3$ | 172.9 ± 10.1** | 138.6 ± 12.4* |
| $10^5$ | 152.4 ± 6.1** | 122.2 ± 4.3* |

Figure 8:
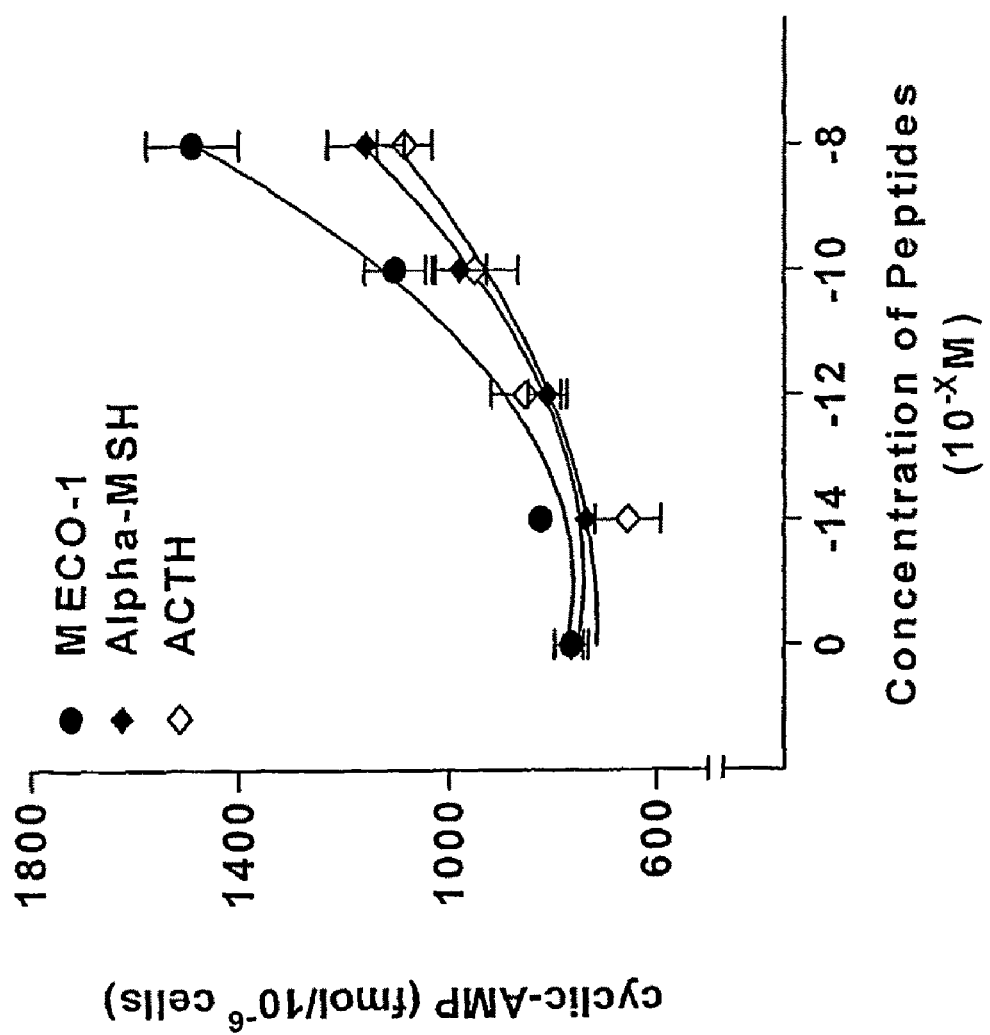
FIG. 8 is a graph of experimental results demonstrating MECO-1 stimulation of cyclic-AMP production. RAW cells were incubated with peptides for 30 minutes at 37° C. in Opti-mem-1 serum-free medium containing 3-isobutyl-1-methylxanthine at 1 mM. Cell lysates were extracted and c-AMP measurements carried out using a commercial kit (c-AMP Biotrack-Immunoassay system, Amersham Biosciences, Piscataway, N.J.) with a c-AMP standard curve as recommended by the suppliers. In the four experiments with MSH alone, stimulation that was statistically significant was noted at $10^{-9}$ M three times and once at $10^{-10}$ M. MECO-1 alone gave positive results at $10^{-10}$ molar in two experiments and at $10^{-9}$ and $10^{-8}$ molar in additional experiments. The only experiment with ACTH is shown above. Any effects at LPS at 4 ng/ml on ligand-stimulated c-AMP and of HMGB1 at a 100 ng/ml in the presence of ligands was quite modest and somewhat inconsistent. These data are consistent with observations in other systems where the sensitivity measuring a biological end point response is one or more log units to the left of the standard curve for c-AMP production which has been interpreted to indicate that downstream pathways are exquisitely sensitive to low levels and small changes in c-AMP concentrations.

The experiment was as described in the legend of FIG. 7 except that HMGB1 were replaced by LPS (10 ng/ml) and anti-receptor antibody was replaced by the agouti, protein, a known inhibitor of α-MSH action via MC1R. NF release by LPS (10 ng/ml) alone: was set at 100%.
**$p < 0.01$ vs. MECO-1,
*$p < 0.05$ vs. α-MSH Post Receptor Pathways. The melanocortin receptors, including MC1R, are typically linked via G-proteins to adenylate cyclase, cAMP, and protein kinase A. In RAW cells, ACTH and MSH stimulated cAMP production in a dose-dependent fashion (FIG. 8). MECO-1 gave very similar results (FIG. 8). At the highest concentrations, the three peptides stimulated cAMP almost to the level achieved by forskolin alone in the same system (data not shown). In one experiment, the addition of anti-MC1R antibody shifted the curve three log units to the right for MECO-1 stimulation of cAMP (data not shown). Co-incubation with LPS at 4 ng/ml or with HMGB1 at 100 ng/ml (six experiments) had little effect on the cAMP stimulation (data not shown).

Figure 9:
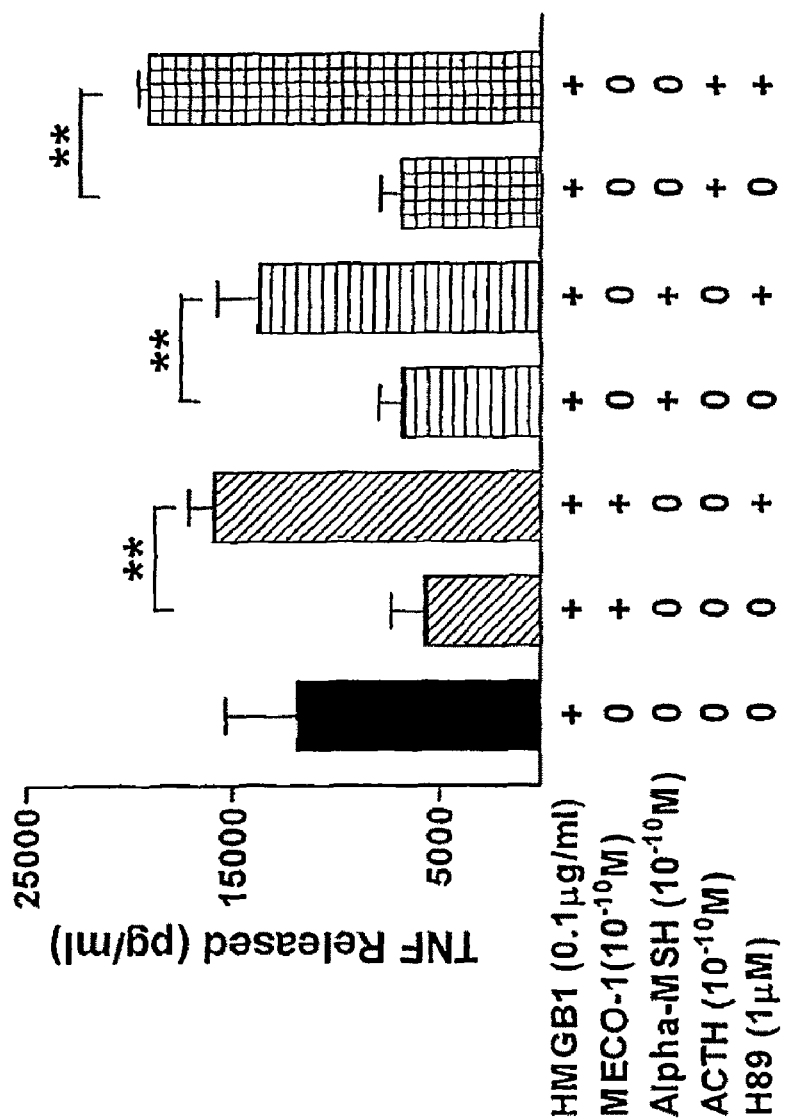
FIG. 9 is a graph of experimental results showing the prevention of MECO-1 activity by inhibition of protein kinase A. RAW cells were incubated for 6 h with HMGB1 (0.1 µg/ml) in the presence or absence of melanocortin peptides at $10^{-10}$ M, as described in the legend to FIGS. 5C and 5D. H89 was present at 1 µM (added 10 min. before other regents). Data represent mean±SEM of two independent experiments performed in duplicate (**p<0.01).
Figure 10:
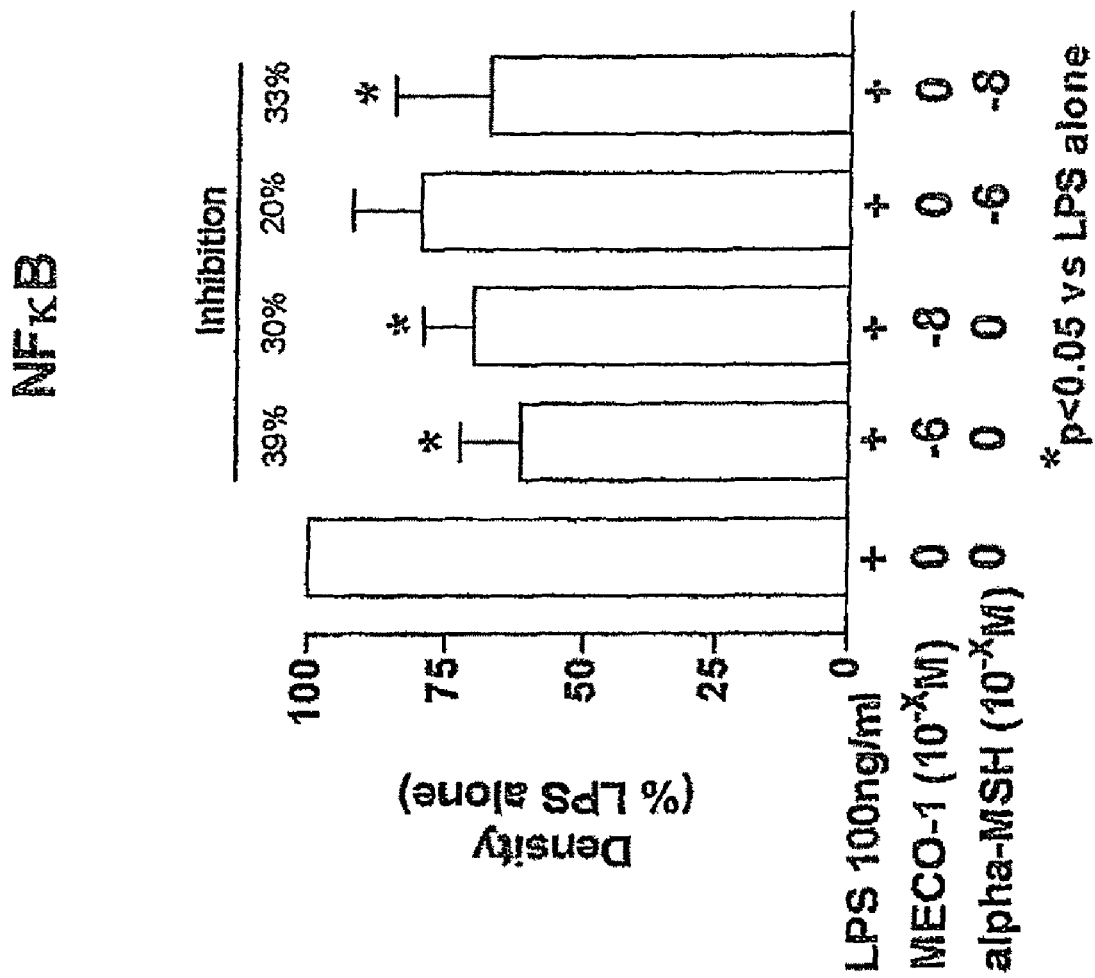
FIG. 10 is a graph of experimental results showing the effect of melanocortin peptides on NF-κB activity. RAW cells were incubated with LPS (100 ng/ml) with or without MECO-1 or α-MSH at $10^{-8}$ M and $10^{-6}$ for 2 hr. Nuclear extracts were mixed with biotin-labeled oligonucleotides containing binding sites for NF-κB and then run on a 4-20% Ready gel TBE gel in an EMSA. Densitometric values for the active transcription factors were obtained using GS-800 Calibrated Densitometer software (Biorad, Hercules, Calif.). Data represent mean±SEM of two separate experiments.
Figure 11:
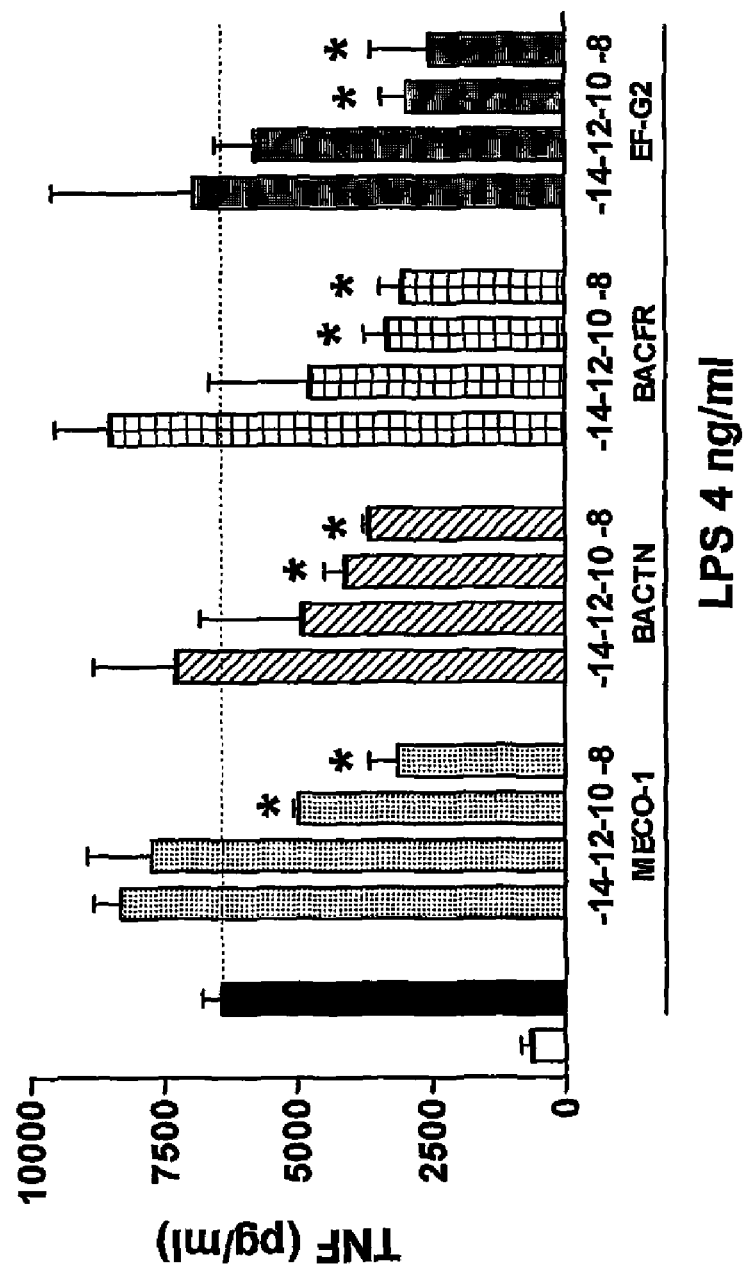
FIG. 11 is a graph showing the activities of bioactive analogues of MECO-1. The experimental conditions with macrophage-like cells were the same as those previously described except that the LPS concentration was 4 ng/ml. In addition to MECO-1, four peptides were prepared that matched that portion of the C-terminus of their own EF-G that seemed to correspond best to MECO-1. BACTN refers to *Bacteroides thetaiotamicron*; BACFR to *Bacteroides fragilis*; EFG-2 refers to human mitochondrial EFG-2. In other experiments, the synthetic peptide based on human mitocliondrial EF-G1 gave results indistinguishable from EF-G2 (data not shown). Shown is a representative experiment. Similar results were observed in four other experiments. In this particular experiment MECO-1 showed effects at 100 pM but not at 1 pM. In most experiments, it was effective at 1 pM. *p<0.05 vs. LPS alone.

Role of Protein Kinase A. To demonstrate the role of protein kinase A, RAW cells were incubated with HMGB1. TNF accumulation was markedly enhanced and the accumulation of TNF was substantially reduced by co-incubation with MECO-1, α-MSH, or ACTH at concentrations in the range of $10^{-12}$-$10^{-8}$ molar. The addition of H89, a specific inhibitor of protein kinase A, abrogated the effects of the three peptides (FIG. 9). Indeed, the accumulation of TNF in the presence of H89 often exceeded that obtained by HMGB1 alone. The results were exceedingly similar when experiments were repeated with freshly obtained peripheral blood mononuclear cells from humans (data not shown).

Effects on Nuclear Factor-κB (NF-κB). Activation of macrophages with enhanced cytokine release is one of the many immune system scenarios that is associated with increases in the activity of NF-κB, a nuclear transcription factor that is a major regulator of cytokine-related events. MECO-1 and α-MSH, under conditions where they attenuated cytokine release from macrophages, were equally active in attenuating the rise in NF-κB activity. This is in accord with results of others who showed that α-MSH mediated anti-inflammatory effects, mediated via the MC1R, were associated with attenuation of NF-kB activation (Catania et al, 2004).

Structure Function: Inhibition of LPS-Stimulated TNF release. Macrophage-like RAW cells in the presence of LPS at 4 ng/ml accumulate about ten-fold more TNF in the medium over six hours. Intact MECO-1 (i.e. 1-33) at 1 pM suppresses TNF accumulation by over 30% and at 10 nM by about 70%. Synthetic fragments of MECO-1 (1-19, 8-27, and 18-33), individually and in combination, were a thousand to ten thousand-fold less active; at 10 nM, we observed suppression of TNF release by about 30%.

MECO-1, the 33 amino acid C-terminus of elongation factor-G (EFG) of *E. coli*, shares structural similarities with the C-termini of EFG's of numerous microorganisms, both prokaryotes and eukaryotes (FIG. 1C). *E. coli* is a minor constituent of normal gut flora in humans. Synthetic replicates of the C-terminus of two of the major representatives of the normal flora, *Bacteroides fragilis* and *Bacteroides thetaiotamicron* were tested. Both were about as active as MECO-1 in suppressing TNF release over the full range of the dose-response curve, despite many amino acid substitutions. For *B. fragilis*, a 33-mer consisting of residues 681-703 shown in table 1C, followed by 704-713=QDKLIKDFES (SEQ ID No: 23), was used. For *B. thetaiotamicron*, a 38-mer consisting of residues 681-703 shown in Table 1C, followed by 704-718 QDKLIKDFEAKQTEE (SEQ ID No: 24) was used.

Similar results were obtained with synthetic replicates made of the C-termini of the EFG's of human mitochondria. (28 amino acids for EFG-1 and 33 amino acids for EFG-2 as shown in FIG. 1B). Both of these EFG's are coded in nuclear DNA but are transported to mitochondria where they function as elongation factors for mitochondrial production of proteins. The C-termini of the mitochondrial EFG's are as similar to each other as each is to the *E coli* structure (FIG. 1B). Synthetic replicates are each as active as MECO-1 in suppressing TNF release over the full range of the dose-response curve, despite many amino acid substitutions.

Discussion

When mice are subjected to cecal ligation and puncture (CLP), an experimental model of perforated appendix, the vast majority die of sepsis within 1-2 weeks (Yang et al., 2004; Catania et al., 2004). α-MSH (melanocyte stimulating hormone), given for three days starting 24 hours after the surgery, rescued the mice in a dose-dependent fashion. MECO-1 was at least as potent as α-MSH in rescuing the mice from lethal sepsis. In most forms of sepsis, including that produced by cecal ligation, the death of the animal is caused by the rich menu of cytokines released from a wide range of cell types of the host. Among the early cytokines, we studied tumor necrosis factor (TNF) and interleukin (IL)-6. Measured at forty hours after cecal ligation, serum levels of both TNF and IL-6 were elevated as expected. The administration of one dose of MSH or MECO-1 at 24-hours reduced the levels of both of these cytokines.

It is known that a very important cytokine contributing to lethality in sepsis is HMGB1 (high mobility group box 1) (Lotze and Tracey, 2005; Yang et al., 2005; Yang et al., 2004). This nucleosomal protein (separate from its role as a transcription factor) is a potent late humoral mediator of death from LPS and sepsis. Blocking HMGB1 with antibody, or blocking its binding to cells with a specific receptor-blocking peptide, rescues animals from lethality even when started as late as 24 hours after the initiation of sepsis (Lotze and Tracey, 2005; Yang et al., 2005; Yang et al., 2004). In this study, both α-MSH and MECO-1 markedly reduced the elevated levels of HMGB1 that are produced by sepsis. We attribute the rescue of the mice to the control of the release of cytokines, in particular, the marked reduction in HMGB1 levels.

In mammals, pro-inflammatory and anti-inflammatory agents are in a tug of war, aiming to overcome microbial invaders and yet prevent the host organism from being killed by the injurious effects of its own innate immune system (Janeway and Medzhitov, 2002; Pasare and Medzhitov, 2004; Hoebe et al., 2004). Typically bacteria are pro-inflammatory. Recognition that *E. coli* releases a potent anti-inflammatory peptide raises the possibility that the microorganisms may likewise generate a mix of both pro- and anti-inflammatory forces. The finding that *E. coli* can produce a potent anti-inflammatory mediator may shed light on another paradox. *E. coli* was used as a representative of the intestinal flora, although it is a minor constituent among the almost 1,000 bacterial species noted among the intestinal microbes (Eckburg et al., 2005; Backhed et al., 2005). The normal intestinal tract is home to up to one hundred trillion microorganisms, exceeding by about 10-fold the total number of cells in the body (Backhed et al., 2005). Yet, the normal intestine, as well as the normal host organism, show little or no untoward response to them (Steinhoff, 2005; Smith and Nagler-Anderson, 2005; Backhed et al., 2005; Chandran et al., 2003; Macdonald and Monteleone, 2005; Abreu et al., 2005). This is in contrast to the vigorous pro-inflammatory response shown to a small number of microbes or even cell-free microbial products in other parts of the body. L. E. Smythies et al. conclude "blood monocytes recruited to the intestinal mucosa retain avid scavenger and host defense functions but acquire profound inflammatory anergy, thereby promoting the absence of inflammation characteristic of normal intestinal mucosa despite the close proximity of immunostimulatory bacteria." (Smythies et al., 2005). The hypothesis from this work is that MECO-1 and possibly other secretory products from the very dense concentration of microorganisms in the gut (among the highest cell densities recorded anywhere) collectively produce anti-inflammatory effects that are able to maintain the normal uninflamed state. Likewise, disruptions in these anti-inflammatory pathways may contribute to inflammatory diseases of the intestine (Backhed et al., 2005; Chandran et al., 2003; Sartor, 1997; Eckmann, 2004; Sartor, 2003). The possible role of bacteria-derived products as pro-inflammatory influences has received a great deal of attention with regard to the major inflammatory bowel diseases, ulcerative colitis and Crohn's disease, as well as other inflammatory diseases such as rheumatoid arthritis (Sartor, 1997). Here we provide a further basis for normal flora as a source of a potent anti-inflammatory influence; loss or interference with this and other anti-inflammatory agents may be contributing to disease processes in the bowel and possibly beyond.

It is postulated here that MECO-1 produces its anti-inflammatory effects by acting locally on cells resident in the GI tract These would include epithelial lining cells, immune cells, secretory cells (exocrine and endocrine) and neural elements. Macdonald and Monteleone, in their discussion of gut antigens in a recent review, catalog numerous mechanisms by which macromolecules can traverse the gut epithelial barrier (Macdonald and Monteleone, 2005). α-MSH is known to produce many of its anti-inflammatory effects centrally (Lipton et al., 1991; Catania et al., 1999). Thus, MECO-1 might act at sites beyond the gut lumen, including possibly the CNS (Gebbers and Laissue, 2004; Garside et al., 2004). The observation that MECO-1 is quite stable in vivo, possibly more so than α-MSH, raises the possibility that MECO-1 may, in addition to its local effects in the gastrointestinal tract, be acting at more distant sites as well. As noted in Results, MECO-1 and α-MSH were equipotent in vitro while MECO-1 appeared to be possibly multifold more effective in the septic mouse.

Pro-inflammatory processes have been implicated seriously in a wider range of abnormal conditions including atherosclerosis and dementia, as well as the cognitive and physical decline with aging (Getz, 2005; Hansson, 2005; McGeer and McGeer, 2004; Yaffe et al., 2004; Wilson et al., 2002). A logical therapeutic approach would be to try to enlist the anti-inflammatory capabilities of MECO-1 and other possible anti-inflammatory agents derived from normal flora.

In mammals in vivo, the melanocortins and their receptors have been implicated in sexual function, behavior, learning, and a wide range of other processes (Cone, 2002). Especially prominent is the role of α-MSH in regulating food intake, energy expenditure, and body weight, with MC4R being much more important than MC3R (Badman and Flier, 2005; Korner and Leibel, 2003). Mutations in only one allele of the gene for MC4R is frequently associated with massive obesity and binge eating (Farooqu and O'Rahilly, 2005). Based on previous work (Backhead et al., 2005; Badman and Flier, 2005), the possibility is raised that these hormone-like agents may be exerting effects on the host's food intake and energy balance, intercalating within the host's own systems of intercellular communication. The POMC gene is expressed in a broad range of cell types as are the cognate convertases that process the peptide precursors into hormones (Cone, 2000). Even more widely distributed are the melanocortin receptors (Cone, 2000). That these receptors are activated by picomolar concentrations of MSH opens the possibility that even very modest amounts of MECO-1 in the systemic circulation may have widespread effects.

MECO-1 is apparently being released in a biologically organized manner from intact bacteria, based on the observations that after inaugurating the culture, melanocortin-like peptides accumulate in the medium very quickly. At the same time the absence of pyrophosphatase, an intracellular enzyme whose appearance in the medium classically reflects death of bacteria, is noted. This is also consistent with the observation that the accumulation of the MECO-1-related peptides slowed as the culture aged, a time when cell death and breakage typically increase. Of note, a process designated as regulated intramembranous proteolysis (Rip), widely described in eukaryotes and prokaryotes, has recently been implicated in intercellular communication (Urban and Freeman, 2002). A recent study showed the functional interchangeability of the intramembranous protease that releases epidermal growth factor ligands in Drosophila and the protease in a gram negative bacterium, *Providencia stuartii*, that generates extracellular signals that regulate the microbes' density dependent growth, part of the quorum sensing process (Gallio et al., 2002).

Pheromones, ligands that signal between two organisms of the same species, are now being widely recognized in microbes. Unicellular eukaryotes, for example, regulate reproduction and feeding, with ligands and receptors that are like mammalian counterparts, e.g. small peptides that bind to seven transmembrane domain activators of GTPases, and also steroid-related ligands that bind to and activate nuclear binding proteins that regulate gene transcription (Bardwell, 2004; Riehl and Toft, 1984).

Pheromones have been described widely in a broad range of bacteria to carry out quorum sensing, a process of intercellular communication that is responsive to cell density. In this way a community of bacteria regulates its behavior and gene expression, including secretion of virulence factors, biofilm formation, reproductive processes, and sporulation (Henke and Bassler, 2004).

There are now multiple examples where these ligands can also affect organisms of another species. The targets may be other bacteria, or unicellular or multicellular eukaryotes. Eavesdropping, deception, antagonism, cooperation and disease modification are among the consequences of the interspecies communication (Schuiling, 2004; Mathesius et al., 2003; Federle and Bassler, 2003; Greenberg, 2003). Molecular signals sent from one organism to activate receptors in another is a pheromone when both are of the same species. When species of sender and recipient are different, the signal molecule is considered to be an allomone or kairomone, when it is beneficial, respectively, to the sender or the recipient (Jerrold Meinwald, personal communication). In this hypothetical construct, MECO-1 would probably qualify as both.

The hypothesis that bacteria at high density in the gut sustain a non-inflammatory environment may also apply to abscesses, in the brain and in other body sites, where again, a large concentrated collection of bacteria often produce few or no signs of inflammation. H.

Houston Merritt in the first edition of his now classic text noted, "the symptoms of brain abscess are essentially the same as those of any (sterile) expanding lesion in the brain. Symptoms of infection are lacking unless the focus which gave rise to the abscess is still active. Not infrequently, the symptoms of an abscess in the cerebral or cerebellum are limited to those resulting in an increase of intracranial pressure." (Merritt, 1955).

It is speculated here that apoptosis may include a similar phenomenon. In addition to the (i) flamboyant lysis of the cell programmed by (ii) a complex interplay of enzymes and other proteins, apoptosis, is characterized by (iii) the remarkable absence of an inflammatory response and (iv) the leak of cytochrome C and other proteins from the mitochondria. Most mitochondrial proteins, whether coded in the mitochondria's own DNA or in nuclear DNA, are thought to have a recent link to bacteria, reflecting current beliefs that the mitochondria are bacterial elements that evolutionarily immigrated and took up permanent residence in eukaryotic cells. The two elongation factors that function within human mitochondria, EF-G1(mt) and EF-G2(mt), (though coded in the nucleus) are more similar in structure to elongation factor G of E. coli and of other bacteria (Bhargava et al., 2004; Hammarsund et al., 2001; Gau et al., 2001; also see FIG. 1 and the paragraph immediately below) than to the human cytoplasmic homologue, elongation factor-2 (EF-2). Interestingly, EF-G1(mt) of humans was found to be active as a translocase in bacterial as well as human ribosomes (Bhargava et al., 2004). A synthetic replicate of the 28 amino acid peptide from the C-terminus of EF-G1(mt), which has 13 amino acids that are the same as in MECO-1, was about as potent as MECO-1 and α-MSH in suppressing the TNF release from macrophage-like (RAW) cells after exposure to lipopolysaccharide at 4 ng per ml (Qiang, X and Roth, J unpublished observations). This fragment is thus a candidate contributor to the anti-inflammatory condition typically associated with apoptosis.

ACTH and α-MSH represent alternative processing of the same precursor and have very similar interactions with four of the melanocortin receptors (all except MC2R). See, e.g., Eberle, 2000; Hruby and Han, 2000. While the primary sequences of amino acids 1-13 are identical in ACTH and α-MSH, the latter has two post-translational moieties, an N-terminal acetyl and a C-terminal amide, that are considered important for full potency of α-MSH. Just like the 14-39 C-terminal peptide of ACTH allows full activity in the absence of the posttranslational moieties, so too the 18-29 C-terminal peptide of MECO-1. Importance cannot be ascribed to the multiple identities and similarities between ACTH 26-38 and amino acids 18-29 in MECO-1 because ACTH 1-24, lacking those overlaps in sequence, is fully as active as ACTH biologically. Because it is invariant in the ACTH, α-MSH, β-MSH, and γ-MSH of all chordates studied (as well as the MSH-A and MSH-B of lamprey and the δ-MSH of dogfish), the HFRW sequence at positions 6-9 of ACTH and α-MSH has been considered canonical. ("The structural feature characterizing all MSH sequences and that of ACTH is the core tetrapeptide His-Phe-Arg-Trp, which is crucial for the interaction with the receptors of these peptides and hence for their biological activity.") (Eberle, 2000). Thus the full bioactivity of MECO-1 has been a surprise. In MECO-1 and in many other bacteria, HFRW is replaced by FLKY, with no identities and three amino acids that are considered similar. Of the five amino acids in α-MSH that are N-terminal of that canonical sequence, four are identical and one is identified as "similar" in MECO-1. Interestingly, experts suggest that α-MSH "residues in positions 1,2,3 (12 and 13) are relatively less important" and that residues 4,5, and 10 may be important in establishing appropriate conformations.

In conclusion, described here is MECO-1, a melanocortin-like peptide released by *Escherichia coli*, that like the mammalian hormones MSH and ACTH, (i) activates melanocortin-1 receptors of mammalian macrophages, (ii) suppresses elements of the host's innate immune system, and (iii) can rescue mice from lethal sepsis.

A scenario is hypothesized here whereby MECO-1 (and its yet undiscovered cousins released from other enteric bacteria) is responsible for important hormone-like signals to one class of melanocortin receptors on enteric macrophages. Hypothesized further is that MECO-1 and other signals such as these may allow the great mass of bacteria in the gut to co-exist in peaceful harmony with the host, especially with its macrophages and other gut associated lymphoid elements.

In addition to discovering a hormone (or more properly, a hormone-like agent), this may be a novel system of intercellular communication between enteric flora and their mammalian hosts. While the system here is newly described, it is built on decades of work on microbial signals, including those included under quorum sensing (Henket and Bassler, 2004; Schuiling, 2004; Mathesius et al., 2003; Federle and Bassler, 2003; Greenberg, 2003), and those that have features like messenger molecules of vertebrates (Macchia et al., 1967; LeRoith et al., 1986; Roth et al., 1986; Lenard, 1992).

EXAMPLE 2

Effect of MECO-1 on Colitis and Other Forms of Inflammatory Bowel Disease

Introduction

Bacteria and their products are highly stimulatory to the host's immune system, activating host cells and stimulating release of cytokines and other pro-inflammatory agents The present studies have shown that bacteria of the type that normally inhabit the gut also produce and release substances that are anti-inflammatory that are able to suppress the pro-inflammatory responses in the host.

Hypotheses

Our hypothesis is that (i) colitis and other inflammatory diseases of the bowel represent an imbalance between the pro-inflammatory and anti-inflammatory forces, and that (ii) the anti-inflammatory agents of bacterial origin [such as *E. coli*-derived MECO-1 described here] contribute significantly to the normal balance and that (iii) these anti-inflammatory agents can be used therapeutically in patients with inflammatory bowel diseases to restore that balance, i.e health.

Receptor for MECO-1-We have shown [in studies reported here] that MECO-1 exercises its anti-inflammatory powers by binding to the melanocortin receptor subtype MC1R, the same receptor that is used by the hormone-like peptide alpha-MSH and other endogenous human peptides.

We have carried out a series of experiments with animal models of colitis that support those hypotheses.

Experiment A. It had recently been observed that mice which have been genetically engineered to lack both copies of their gene for MC1R seemed normal until given DSS, a widely used laboratory stimulator of a mild colitis. In the animals missing the receptor the DSS colitis was fulminating and often deadly (Maaser et al., 2006).

A complementary experiment was performed. Normal mice were given the same load of colitis stimulator DSS. It was reasoned that if the lack of MC1R receptor provoked severe colitis, then normal mice harboring normal receptor could be pushed into severe DSS colitis by inactivating MECO-1 and the other similar endogenous activators of the MC1R present in the gut. When these DSS treated mice were infused intrarectally twice daily with anti-MECO-1 antibody, the colitis was much more severe than the colitis in mice treated intrarectally with a control serum. It is postulated that the anti-MECO-1 antibody inactivates MECO-1 as well as comparable MECO-1-like anti-inflammatory peptides produced by other bacteria residing in the gut. It is concluded that DSS, typically a stimulator of a mild colitis, is held in check in part by the bacterially derived anti-inflammatory peptides acting on the MC1R. Inadequate supplies of these anti-inflammatory peptides leads to very severe colitis.

Experiment B. The above experiments were extended to other models of colitis. Mice were administered orally a toxigenic bacterium derived from *B. fragilis*, which typically produces a colitis that is more severe than the colitis induced by a non-toxigenic variant of the same organism which in turn is worse than that observed in the control buffer-treated mice. Loss of weight and histological changes in the bowel are the measures of the severity of the colitis, with death as a further end point. In every group, the intrapritoneal injection of MECO-1 antibody caused an aggravation of the colitis (using normal non-immune serum as control). These results are consistent with the hypothesis that anti-MECO-1 antibody, by binding and neutralizing *E. coli*-derived MECO-1 and similar anti-inflammatory agents from other bacteria in the gut, tilts the balance to the pro-inflammatory side. This is consistent with the therapeutic applications proposed for colitis, other inflammatory disorders of the gastrointestinal tract, and for the many other diseases where inflammatory processes play a significant role in the pathophysiology.

Experiment C: To complement the studies in Experiment B where anti-MECO antibody aggravated the colitis, it was hypothesized that administration of MECO-1 would ameliorate the colitis. In this set of studies, the colitis was enhanced by adding DSS 2% to the drinking water for 5 days before administering buffer, non-toxigenic bacteria, or toxigenic bacteria. In the buffer-treated animals and non-toxigenic bacteria groups, the colitis was ameliorated by intraperitoneal injections of MECO-1, as predicted. In the group treated with toxigenic bacteria on a background of DSS administration, the mortality was swift and very widespread.

EXAMPLE 3

Regulation of Food Intake and Energy Balance with MECO-1

Background and Introduction

In addition to the immune linked effects of melanocortins and the melanocortin receptors, recall (i) the central role of α-MSH and melanocortin 4 receptors (MC4R) in food intake and body weight regulation and (ii) the wide open (fenestrated) capillaries that are the gateway to the hypothalamic regions of the brain where the food intake-linked MC4R receptors reside. α-MSH and MC4R in the hypothalamus act to limit food intake directly and also indirectly by suppressing the NPY system that drives eating.

The relevance of α-MSH and MC4R to energy balance is highlighted by patients with mutations in the gene for MC4R who show massive obesity and binge eating. Likewise, patients with mutations in pro-opiomelanocortin, the parent molecule of α-MSH, also show massive obesity.

Recent studies have shown access of peptides in gut into the general circulation. There is also likely access of melanocortins from gut microorganisms into blood and from there to hypothalamus and related areas of brain, where they contribute to signals that dampen food intake. Such pathways might be part of mechanisms to account for some of the metabolic differences between germ-free rodents and their bacteria-colonized counterparts. Counterintuitively, but consistent with the above findings and hypotheses, the germ-free rodents consume 20% more calories than mice with microbial flora. Likewise, antibiotic-treated animals gain more weight.

Experiment A. A molecular biological construct of the melanocortin-4 receptor, MC4R, was transfected into HEK tissue culture cells. In those cells, MECO-1 was as active as α-MSH in stimulating that receptor, measured as activation of luciferase linked to the MC4R pathway. It is concluded that MECO-1, in addition to mimicking α-MSH at the MC1R and MC2R receptors, mimics α-MSH at the MC4R receptor.

MC3R is another melanocortin receptor that has been related to satiety and energy balance in vivo. MECO-1, when tested with MC3R in a transfection system similar to the system used to study MC4R, gave activity very similar to that of α-MSH. It is concluded that MECO-1 (and by inference to other EFG-derived MECO-like peptides of other systems) activates MC1R, MC2R, MC3R and MC4R in a manner very similar to that described for α-MSH.

Figure 12A:
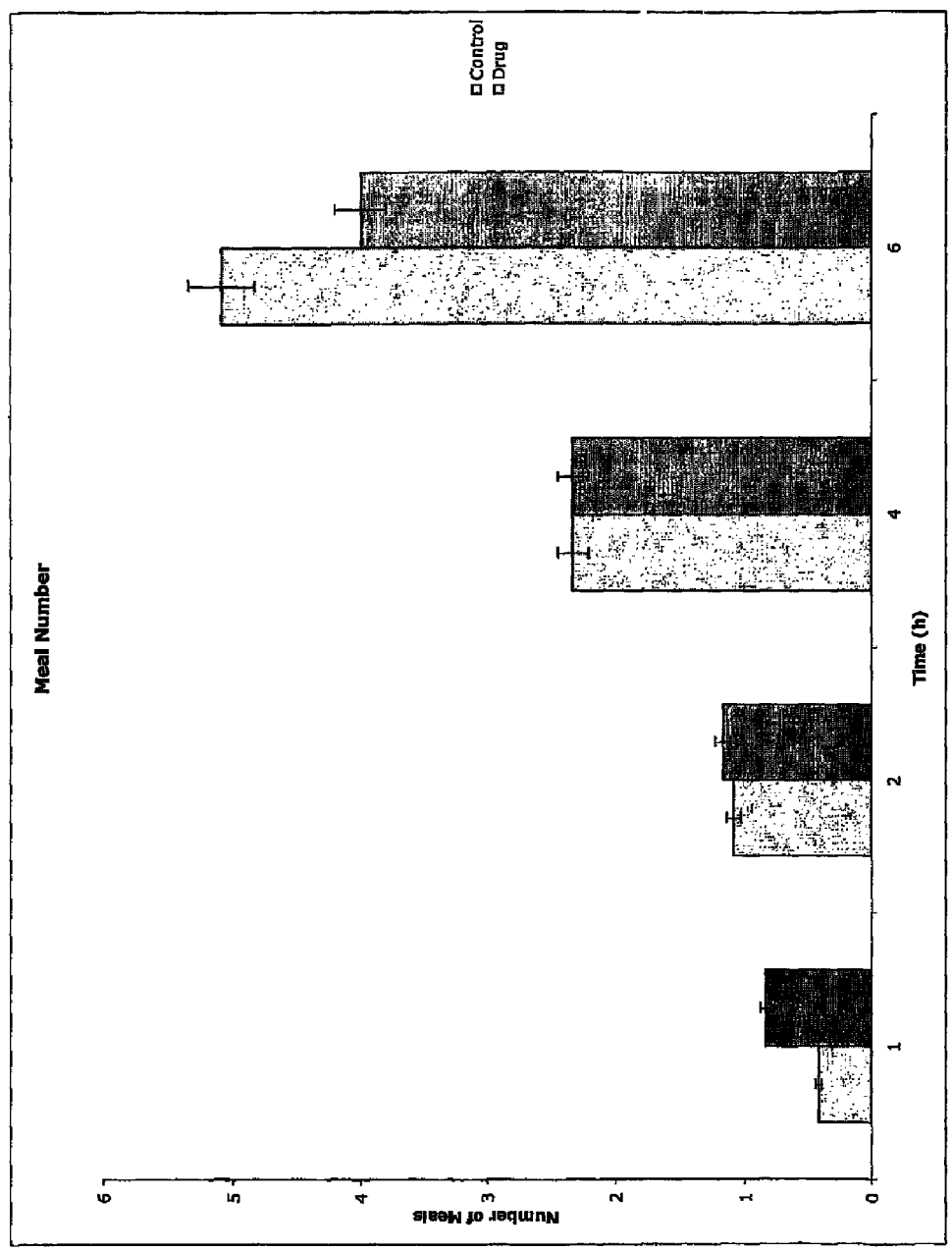
FIG. 12 is graphs showing the effect of MECO-1 on suppression of food intake in mice. Panel A shows the effect of MECO-1 on the cumulative number of meals. The MECO-1 treated mice (right handed member of each pair of bars) have a slight increase in meal number at 1 hour but by six hours have a modest (roughly 20%) reduction. Panel B shows the effect MECO-1 on meal size. The mice treated with MECO-1 (right half of bar pairs) show a marked diminution in meal size at 1 hr, 2 hrs, and 6 hrs. That the major mechanism for diminution in total food intake is a diminution in meal size is a hallmark of melanocortins and speaks to the biological relevance of the observations. Panel C shows the cumulative food intake by MECO-1 treated mice. This figure shows the reduced cumulative intake of food over six hours by mice who received a dose of MECO-1 into the arcuate nucleus of the hypothalamus, in comparison with mice who received buffer control. This result is very similar to results with α-MSH, the native signal.
Figure 12B:
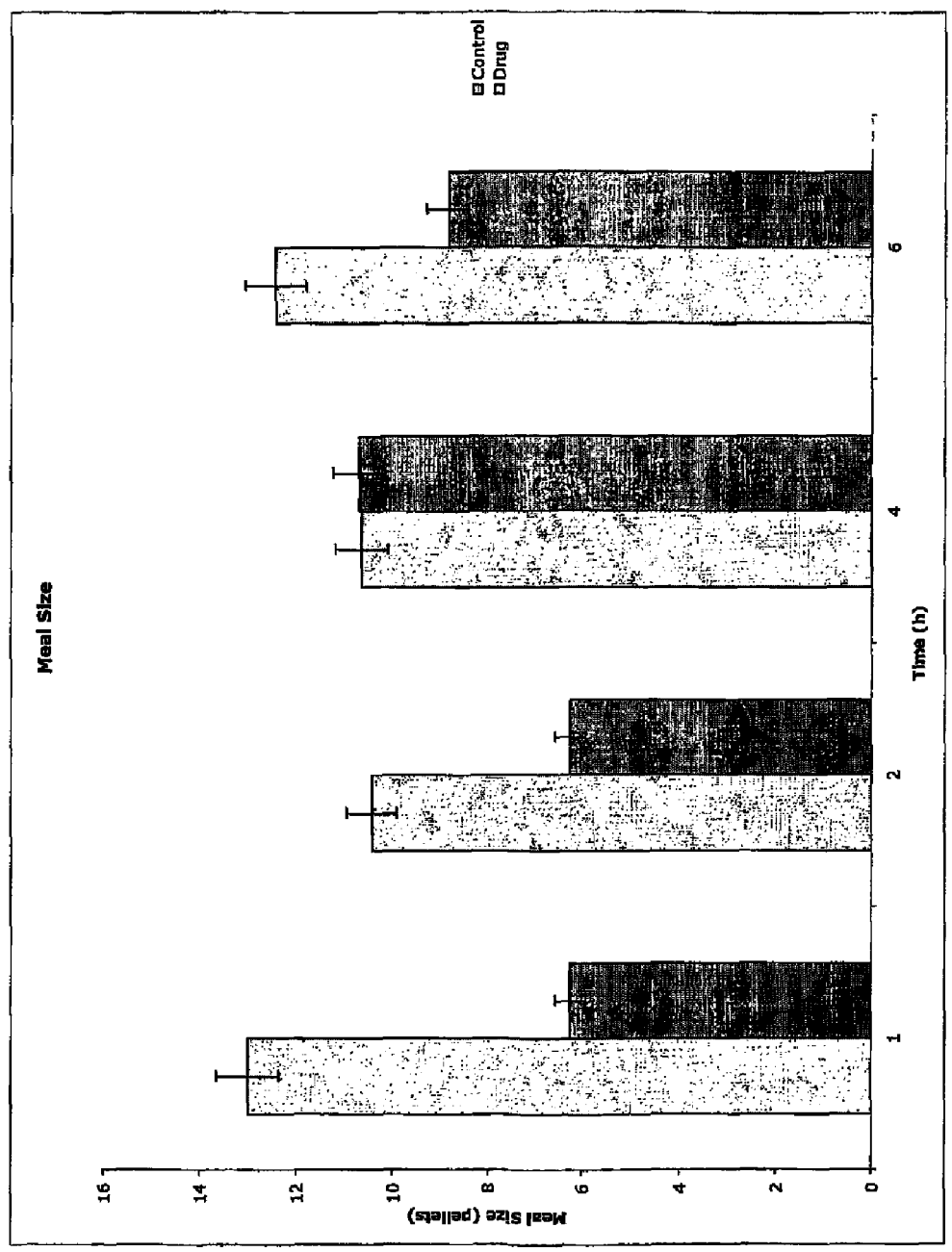
Figure 12C:
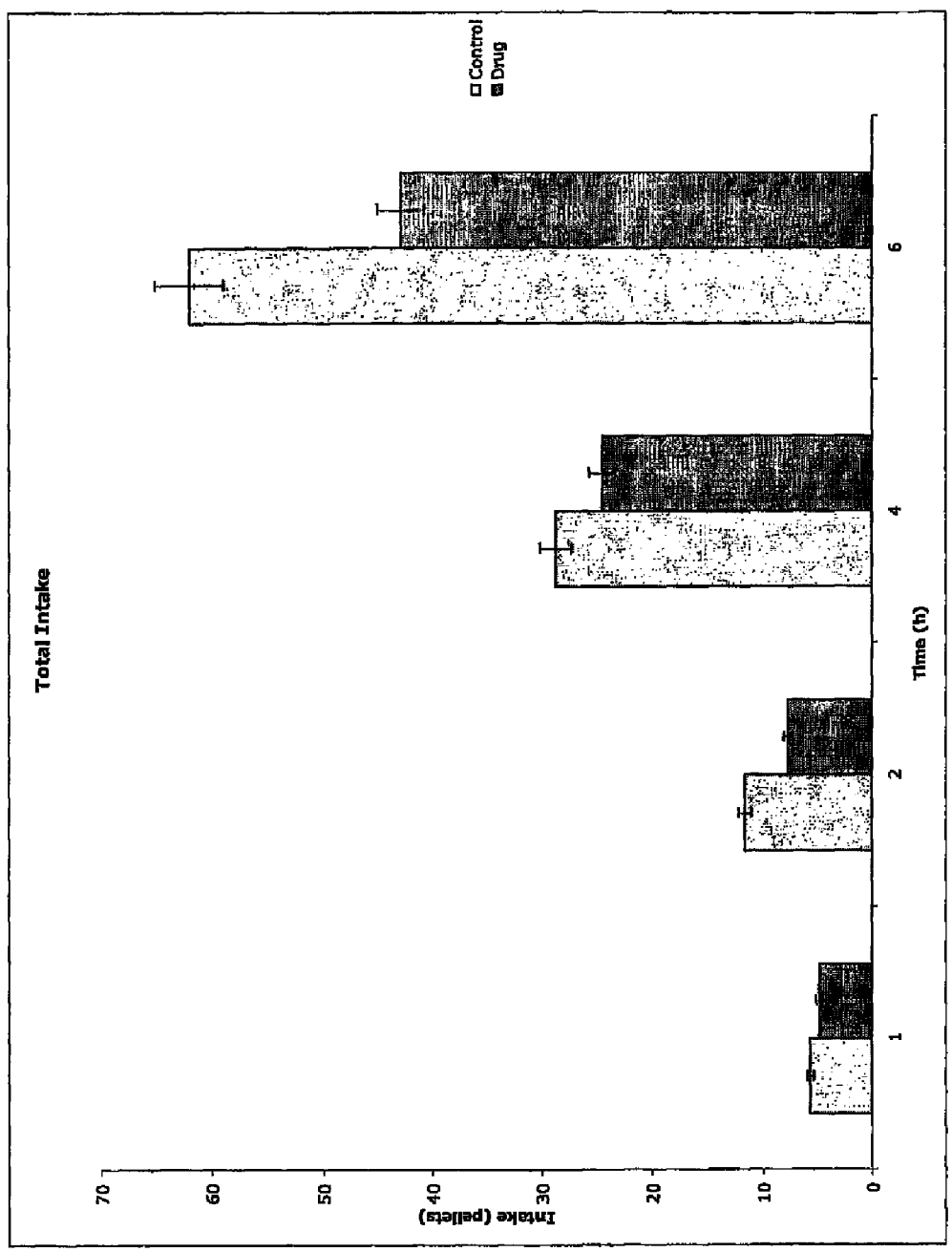

Experiment B. To show the relevance of this observation in cell culture to the in vivo world, we studied mice who are normal in every way except that they have tiny plastic cannulas that open at the site of the arcuate nucleus of the hypothalamus, the part of the brain most concerned with starting and stopping of eating. When minute amounts of α-MSH are infused, the animals eat as often but consume about half as many pellets per "meal" resulting in a decrease in overall food intake (FIG. 12). MECO-1 produces a result that is indistinguishable from that observed with α-MSH, which is the normal signal molecule in this aspect of satiety. Note that this area of brain, unlike many other brain regions, has open access to the blood and to substances in blood.

These data are consistent with the conclusion that MECO-1 and MECO-1 like peptides from microorganisms and other sources such as mitochondria can substitute fully for α-MSH. Each of these MECO-1 like agents may represent a more cost effective and efficient agent for the full range of therapies that have been proposed for α-MSH and its congeners.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID Nos

SEQ ID NO: 1-MECO-1

SLTKGRASYTMEFLKYDEAPSNVAQAVIEARGK

SEQ ID NO: 2-consensus sequence of EF-G sequence from various elongation factors corresponding to MECO-1

(S/T)(L/Q/C)(T/S)(K/E/G/Q/S)G(R/S/K)(A/G)(S/E/T)(Y/H/F)(T/S/A/I)
(M/L)(E/K)(F/Y/L/P)(L/S/K/A)(K/R/T/E/S/H)Y(D/N/E/A/Q)(E/P/A/D/L)
(A/C/M/V)(P/L/N)(S/P/N/K/T)(N/S/Q)(V/T/D/I)(A/Q)(Q/E/N/K/D/A)
(A/D/T/S/K/E)(V/L/I)(I/L)(E/N/A/K)(A/R/S/D)(R/F)(G/S/E)(K/G/S/A)

SEQ ID NO: 3-human EF-G1 sequence corresponding to MECO-1

SCTEGKGEYTMEYSRYQPCLPSTQEDVI

SEQ ID NO: 4-human EF-G2 sequence corresponding to MECO-1

TLTSGSATFALELSTYQAMNPQDQNTLLNRRSGLT

SEQ ID NO: 5-*Salmonella typhimurium* EF-G sequence corresponding to MECO-1

SLTKGRASYTMEFLKYDDAPNNVAQAVIEARGK

SEQ ID NO: 6-*Erwinia carotovora* EF-G sequence corresponding to MECO-1

SLTKGRASYSMEFLKYDDAPNNVAQAVIEARGK

SEQ ID NO: 7-*Photorhabdus luminescens* EF-G sequence corresponding to MECO-1

SQTQGRASYSMEFLKYNEAPSNVAQAIIEAR

SEQ ID NO: 8-*Yersinia pseudotuberculosis* EF-G sequence corresponding to MECO-1

SQTQGRASYSMEFLEYAEAPSNVAKAVIEARGK

SEQ ID NO: 9-*Coxiella burnetii* EF-G sequence corresponding to MECO-1

SLSQGRATYTMEFLKYAEAPSNIAEAII

SEQ ID NO: 10-*Bordetella pertussis* EF-G sequence corresponding to MECO-1

SLTQGRATYTMEFKHYAEAPKNVADEVIAARGK

SEQ ID NO: 11-*Pasteurella multocida* EF-G sequence corresponding to MECO-1

SQTQGRASYSMEPLKYAEAPKNVADAIIEAR

APPENDIX-continued

SEQ ID Nos

SEQ ID NO: 12-*Candidatus blochmannia floridanus* EF-G sequence corresponding to MECO-1

SQTQGRASHSMEFLKYNEVPNNIAQSIIESR

SEQ ID NO: 13-*Mannheimia succiniciproducens* sequence corresponding to MECO-1

SQTQGRASYSMEPLKYAEAPTSVAAAVIEAR

SEQ ID NO: 14-*E. coli* EF-G sequence

```
  1 marttpiary rnigisahid agktttteri lfytgvnhki gevhdgaatm dwmeqeqerg
 61 ititsaatta fwsgmakqye phriniidtp ghvdftieve rsmrvldgav mvycavggvq
121 pqsetvwrqa nkykvpriaf vnkmdrmgan flkvvnqikt rlganpvplq laigaeehft
181 gvvdlvkmka inwndadqgv tfeyedipad mvelanewhq nliesaaeas eelmekylgg
241 eelteaeikg alrqrvlnne iilvtcgsaf knkgvqamld avidylpspv dvpaingild
301 dgkdtpaerh asddepfsal afkiatdpfv gnltffrvys qvvnsgdtvl nsvkaarerf
361 grivqmhank reeikevrag diaaaiglkd vttgdtlcdp dapiilerme fpepvisiav
421 epktkadqek mglalgrlak edpsfrvwtd eesnqtiiag mgelhldiiv drmkrefnve
481 anvgkpqvay retirqkvtd vegkhakqsg grgqyghvvi dmyplepgsn pkgyefindi
541 kggvipgeyi pavdkgiqeq lkagplagyp vvdmgirlhf gsyhdvdsse lafklaasia
601 fkegfkkakp vllepimkve vetpeentgd vigdlsrrrg mlkgqesevt gvkihaevpl
661 semfgyatql rsltkgrasy tmeflkydea psnvaqavie argk
```

SEQ ID NO: 15-*Shigella flexneri* sequence corresponding to MECO-1

SLTKGRASYTMEFLKYDEAPSNVAQAVIEARGK

SEQ ID NO: 16-*Bacterioides fragilis* sequence corresponding to MECO-1

SLTGGRASFIMKFASYELVPSDVQDKLIKDFES

SEQ ID NO: 17-*Bacterioides thetaiotamicron* sequence corresponding to MECO-1

SLTGGRASFIMKFASYELVPTDVQDKLIKDFEA

SEQ ID NO: 18-consensus of EF-G sequence from various elongation factors corresponding to MECO-1. Included are only amino acids where at least 2 among the sequences compared.

S(L/Q)T(K/Q/G)GRA(S/T)(Y/F)(T/S/I)M(E/K)F(L/S/A)(K/S)Y(D/N/E/A/Q)
(E/L/D)(A/V)P(S/P/N/K/T)(N/S/D)(V/I)(A/Q)(Q/E/D)(A/K)(V/L/I)I(E/K)
(A/D)(R/F)(G/E)K

---

What is claimed is:

1. An isolated and purified peptide of less than 100 amino acids having melanocyte stimulating hormone (MSH) activity, wherein the peptide comprises or consists of the amino acid sequence of any one of SEQ ID NO: 1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17.

2. The peptide of claim 1, wherein the peptide comprises the amino acid sequence of any one of SEQ ID NO: 1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17.

3. The peptide of claim 1, wherein the peptide comprises the amino acid sequence of SEQ ID NO: 1.

4. The peptide of claim 1, wherein the peptide consists of the amino acid sequence of any one of SEQ ID NO: 1, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO:16, or SEQ ID NO:17.

5. The peptide of claim 1, consisting of the amino acid sequence of SEQ ID NO: 1.

6. An isolated and purified peptide of 33 amino acids or less, wherein the peptide comprises an amino acid sequence of SEQ ID NO:2, wherein the peptide has melanocyte stimulating hormone (MSH) activity.

7. The peptide of claim 6, comprising an amino acid sequence of SEQ ID NO:18.

* * * * *

SEQUENCE LISTING

<160> NUMBER OF SEQ ID NOS: 24

<210> SEQ ID NO 1
<211> LENGTH: 33
<212> TYPE: PRT
<213> ORGANISM: Escherichia coli

<400> SEQUENCE: 1

```
Ser Leu Thr Lys Gly Arg Ala Ser Tyr Thr Met Glu Phe Leu Lys Tyr
1               5                   10                  15

Asp Glu Ala Pro Ser Asn Val Ala Gln Ala Val Ile Glu Ala Arg Gly
            20                  25                  30

Lys
```

<210> SEQ ID NO 2
<211> LENGTH: 33
<212> TYPE: PRT
<213> ORGANISM: unknown
<220> FEATURE:
<223> OTHER INFORMATION: consensus sequence of EF-G sequence from -continued

```
          various elongation factors corresponding to MECO-1
<220> FEATURE:
<221> NAME/KEY: misc_feature
<222> LOCATION: (1)..(1)
<223> OTHER INFORMATION: X= S or T
<220> FEATURE:
<221> NAME/KEY: misc_feature
<222> LOCATION: (2)..(2)
<223> OTHER INFORMATION: X= L, Q or C
<220> FEATURE:
<221> NAME/KEY: misc_feature
<222> LOCATION: (3)..(3)
<223> OTHER INFORMATION: X= T or S
<220> FEATURE:
<221> NAME/KEY: misc_feature
<222> LOCATION: (4)..(4)
<223> OTHER INFORMATION: X= K, E, G, Q or S
<220> FEATURE:
<221> NAME/KEY: misc_feature
<222> LOCATION: (6)..(6)
<223> OTHER INFORMATION: X= R, S or K
<220> FEATURE:
<221> NAME/KEY: misc_feature
<222> LOCATION: (7)..(7)
<223> OTHER INFORMATION: X= A or G
<220> FEATURE:
<221> NAME/KEY: misc_feature
<222> LOCATION: (8)..(8)
<223> OTHER INFORMATION: X= S, E or T
<220> FEATURE:
<221> NAME/KEY: misc_feature
<222> LOCATION: (9)..(9)
<223> OTHER INFORMATION: X= Y, H or F
<220> FEATURE:
<221> NAME/KEY: misc_feature
<222> LOCATION: (10)..(10)
<223> OTHER INFORMATION: X= T, S, A or I
<220> FEATURE:
<221> NAME/KEY: misc_feature
<222> LOCATION: (11)..(11)
<223> OTHER INFORMATION: X= M or L
<220> FEATURE:
<221> NAME/KEY: misc_feature
<222> LOCATION: (12)..(12)
<223> OTHER INFORMATION: X= E or K
<220> FEATURE:
<221> NAME/KEY: misc_feature
<222> LOCATION: (13)..(13)
<223> OTHER INFORMATION: X= F, Y, L or P
<220> FEATURE:
<221> NAME/KEY: misc_feature
<222> LOCATION: (14)..(14)
<223> OTHER INFORMATION: X= L, S, K or A
<220> FEATURE:
<221> NAME/KEY: misc_feature
<222> LOCATION: (15)..(15)
<223> OTHER INFORMATION: X= K, R, T, E, S or H
<220> FEATURE:
<221> NAME/KEY: misc_feature
<222> LOCATION: (17)..(17)
<223> OTHER INFORMATION: X= D, N, E, A or Q
<220> FEATURE:
<221> NAME/KEY: misc_feature
<222> LOCATION: (18)..(18)
<223> OTHER INFORMATION: X= E, P, A, D or L
<220> FEATURE:
<221> NAME/KEY: misc_feature
<222> LOCATION: (19)..(19)
<223> OTHER INFORMATION: X= A, C, M or V
<220> FEATURE:
<221> NAME/KEY: misc_feature
<222> LOCATION: (20)..(20)
<223> OTHER INFORMATION: X= P, L or N
<220> FEATURE:
<221> NAME/KEY: misc_feature
<222> LOCATION: (21)..(21)
<223> OTHER INFORMATION: X= S, P, N, K or T
<220> FEATURE:
<221> NAME/KEY: misc_feature
<222> LOCATION: (22)..(22)
```

```
<223> OTHER INFORMATION: X= N, S or Q
<220> FEATURE:
<221> NAME/KEY: misc_feature
<222> LOCATION: (23)..(23)
<223> OTHER INFORMATION: X= V, T, D or I
<220> FEATURE:
<221> NAME/KEY: misc_feature
<222> LOCATION: (24)..(24)
<223> OTHER INFORMATION: X= A or Q
<220> FEATURE:
<221> NAME/KEY: misc_feature
<222> LOCATION: (25)..(25)
<223> OTHER INFORMATION: X= Q, E, N, K, D or A
<220> FEATURE:
<221> NAME/KEY: misc_feature
<222> LOCATION: (26)..(26)
<223> OTHER INFORMATION: X= A, D, T, S, K or E
<220> FEATURE:
<221> NAME/KEY: misc_feature
<222> LOCATION: (27)..(27)
<223> OTHER INFORMATION: X= V, L or I
<220> FEATURE:
<221> NAME/KEY: misc_feature
<222> LOCATION: (28)..(28)
<223> OTHER INFORMATION: X= I or L
<220> FEATURE:
<221> NAME/KEY: misc_feature
<222> LOCATION: (29)..(29)
<223> OTHER INFORMATION: X= E, N, A or K
<220> FEATURE:
<221> NAME/KEY: misc_feature
<222> LOCATION: (30)..(30)
<223> OTHER INFORMATION: X= A, R, S or D
<220> FEATURE:
<221> NAME/KEY: misc_feature
<222> LOCATION: (31)..(31)
<223> OTHER INFORMATION: X= R or F
<220> FEATURE:
<221> NAME/KEY: misc_feature
<222> LOCATION: (32)..(32)
<223> OTHER INFORMATION: X= G, S or E
<220> FEATURE:
<221> NAME/KEY: misc_feature
<222> LOCATION: (33)..(33)
<223> OTHER INFORMATION: X= K, G, S or A

<400> SEQUENCE: 2

Xaa Xaa Xaa Xaa Gly Xaa Xaa Xaa Xaa Xaa Xaa Xaa Xaa Xaa Xaa Tyr
1               5                   10                  15

Xaa Xaa Xaa Xaa Xaa Xaa Xaa Xaa Xaa Xaa Xaa Xaa Xaa Xaa Xaa
            20                  25                  30

Xaa

<210> SEQ ID NO 3
<211> LENGTH: 28
<212> TYPE: PRT
<213> ORGANISM: Homo sapiens

<400> SEQUENCE: 3

Ser Cys Thr Glu Gly Lys Gly Glu Tyr Thr Met Glu Tyr Ser Arg Tyr
1               5                   10                  15

Gln Pro Cys Leu Pro Ser Thr Gln Glu Asp Val Ile
            20                  25

<210> SEQ ID NO 4
<211> LENGTH: 35
<212> TYPE: PRT
<213> ORGANISM: Homo sapiens

<400> SEQUENCE: 4

Thr Leu Thr Ser Gly Ser Ala Thr Phe Ala Leu Glu Leu Ser Thr Tyr
1               5                   10                  15
```

```
Gln Ala Met Asn Pro Gln Asp Gln Asn Thr Leu Leu Asn Arg Arg Ser
            20                  25                  30
Gly Leu Thr
        35

<210> SEQ ID NO 5
<211> LENGTH: 33
<212> TYPE: PRT
<213> ORGANISM: Salmonella typhimurium

<400> SEQUENCE: 5

Ser Leu Thr Lys Gly Arg Ala Ser Tyr Thr Met Glu Phe Leu Lys Tyr
1               5                   10                  15
Asp Asp Ala Pro Asn Asn Val Ala Gln Ala Val Ile Glu Ala Arg Gly
            20                  25                  30
Lys

<210> SEQ ID NO 6
<211> LENGTH: 33
<212> TYPE: PRT
<213> ORGANISM: Erwinia carotovora

<400> SEQUENCE: 6

Ser Leu Thr Lys Gly Arg Ala Ser Tyr Ser Met Glu Phe Leu Lys Tyr
1               5                   10                  15
Asp Asp Ala Pro Asn Asn Val Ala Gln Ala Val Ile Glu Ala Arg Gly
            20                  25                  30
Lys

<210> SEQ ID NO 7
<211> LENGTH: 31
<212> TYPE: PRT
<213> ORGANISM: Photorhabdus luminescens

<400> SEQUENCE: 7

Ser Gln Thr Gln Gly Arg Ala Ser Tyr Ser Met Glu Phe Leu Lys Tyr
1               5                   10                  15
Asn Glu Ala Pro Ser Asn Val Ala Gln Ala Ile Ile Glu Ala Arg
            20                  25                  30

<210> SEQ ID NO 8
<211> LENGTH: 33
<212> TYPE: PRT
<213> ORGANISM: Yersinia pseudotuberculosis

<400> SEQUENCE: 8

Ser Gln Thr Gln Gly Arg Ala Ser Tyr Ser Met Glu Phe Leu Glu Tyr
1               5                   10                  15
Ala Glu Ala Pro Ser Asn Val Ala Lys Ala Val Ile Glu Ala Arg Gly
            20                  25                  30
Lys

<210> SEQ ID NO 9
<211> LENGTH: 28
<212> TYPE: PRT
<213> ORGANISM: Coxiella burnetii

<400> SEQUENCE: 9

Ser Leu Ser Gln Gly Arg Ala Thr Tyr Thr Met Glu Phe Leu Lys Tyr
1               5                   10                  15
```

```
Ala Glu Ala Pro Ser Asn Ile Ala Glu Ala Ile Ile
            20                  25
```

<210> SEQ ID NO 10
<211> LENGTH: 33
<212> TYPE: PRT
<213> ORGANISM: Bordetella pertussis

<400> SEQUENCE: 10

```
Ser Leu Thr Gln Gly Arg Ala Thr Tyr Thr Met Glu Phe Lys His Tyr
1               5                   10                  15

Ala Glu Ala Pro Lys Asn Val Ala Asp Glu Val Ile Ala Ala Arg Gly
            20                  25                  30

Lys
```

<210> SEQ ID NO 11
<211> LENGTH: 31
<212> TYPE: PRT
<213> ORGANISM: Pasteurella multocida

<400> SEQUENCE: 11

```
Ser Gln Thr Gln Gly Arg Ala Ser Tyr Ser Met Glu Pro Leu Lys Tyr
1               5                   10                  15

Ala Glu Ala Pro Lys Asn Val Ala Asp Ala Ile Ile Glu Ala Arg
            20                  25                  30
```

<210> SEQ ID NO 12
<211> LENGTH: 31
<212> TYPE: PRT
<213> ORGANISM: Candidatus blochmannia floridanus

<400> SEQUENCE: 12

```
Ser Gln Thr Gln Gly Arg Ala Ser His Ser Met Glu Phe Leu Lys Tyr
1               5                   10                  15

Asn Glu Val Pro Asn Asn Ile Ala Gln Ser Ile Ile Glu Ser Arg
            20                  25                  30
```

<210> SEQ ID NO 13
<211> LENGTH: 31
<212> TYPE: PRT
<213> ORGANISM: Mannheimia succiniciproducens

<400> SEQUENCE: 13

```
Ser Gln Thr Gln Gly Arg Ala Ser Tyr Ser Met Glu Pro Leu Lys Tyr
1               5                   10                  15

Ala Glu Ala Pro Thr Ser Val Ala Ala Ala Val Ile Glu Ala Arg
            20                  25                  30
```

<210> SEQ ID NO 14
<211> LENGTH: 704
<212> TYPE: PRT
<213> ORGANISM: Escherichia coli

<400> SEQUENCE: 14

```
Met Ala Arg Thr Thr Pro Ile Ala Arg Tyr Arg Asn Ile Gly Ile Ser
1               5                   10                  15

Ala His Ile Asp Ala Gly Lys Thr Thr Thr Thr Glu Arg Ile Leu Phe
            20                  25                  30

Tyr Thr Gly Val Asn His Lys Ile Gly Glu Val His Asp Gly Ala Ala
        35                  40                  45

Thr Met Asp Trp Met Glu Gln Glu Gln Glu Arg Gly Ile Thr Ile Thr
    50                  55                  60
```

```
Ser Ala Ala Thr Thr Ala Phe Trp Ser Gly Met Ala Lys Gln Tyr Glu
 65                  70                  75                  80

Pro His Arg Ile Asn Ile Ile Asp Thr Pro Gly His Val Asp Phe Thr
                 85                  90                  95

Ile Glu Val Glu Arg Ser Met Arg Val Leu Asp Gly Ala Val Met Val
            100                 105                 110

Tyr Cys Ala Val Gly Gly Val Gln Pro Gln Ser Glu Thr Val Trp Arg
        115                 120                 125

Gln Ala Asn Lys Tyr Lys Val Pro Arg Ile Ala Phe Val Asn Lys Met
    130                 135                 140

Asp Arg Met Gly Ala Asn Phe Leu Lys Val Val Asn Gln Ile Lys Thr
145                 150                 155                 160

Arg Leu Gly Ala Asn Pro Val Pro Leu Gln Leu Ala Ile Gly Ala Glu
                165                 170                 175

Glu His Phe Thr Gly Val Val Asp Leu Val Lys Met Lys Ala Ile Asn
            180                 185                 190

Trp Asn Asp Ala Asp Gln Gly Val Thr Phe Glu Tyr Glu Asp Ile Pro
        195                 200                 205

Ala Asp Met Val Glu Leu Ala Asn Glu Trp His Gln Asn Leu Ile Glu
    210                 215                 220

Ser Ala Ala Glu Ala Ser Glu Glu Leu Met Glu Lys Tyr Leu Gly Gly
225                 230                 235                 240

Glu Glu Leu Thr Glu Ala Glu Ile Lys Gly Ala Leu Arg Gln Arg Val
                245                 250                 255

Leu Asn Asn Glu Ile Ile Leu Val Thr Cys Gly Ser Ala Phe Lys Asn
            260                 265                 270

Lys Gly Val Gln Ala Met Leu Asp Ala Val Ile Asp Tyr Leu Pro Ser
        275                 280                 285

Pro Val Asp Val Pro Ala Ile Asn Gly Ile Leu Asp Asp Gly Lys Asp
    290                 295                 300

Thr Pro Ala Glu Arg His Ala Ser Asp Asp Glu Pro Phe Ser Ala Leu
305                 310                 315                 320

Ala Phe Lys Ile Ala Thr Asp Pro Phe Val Gly Asn Leu Thr Phe Phe
                325                 330                 335

Arg Val Tyr Ser Gly Val Val Asn Ser Gly Asp Thr Val Leu Asn Ser
            340                 345                 350

Val Lys Ala Ala Arg Glu Arg Phe Gly Arg Ile Val Gln Met His Ala
        355                 360                 365

Asn Lys Arg Glu Glu Ile Lys Glu Val Arg Ala Gly Asp Ile Ala Ala
    370                 375                 380

Ala Ile Gly Leu Lys Asp Val Thr Thr Gly Asp Thr Leu Cys Asp Pro
385                 390                 395                 400

Asp Ala Pro Ile Ile Leu Glu Arg Met Glu Phe Pro Glu Pro Val Ile
                405                 410                 415

Ser Ile Ala Val Glu Pro Lys Thr Lys Ala Asp Gln Glu Lys Met Gly
            420                 425                 430

Leu Ala Leu Gly Arg Leu Ala Lys Glu Asp Pro Ser Phe Arg Val Trp
        435                 440                 445

Thr Asp Glu Glu Ser Asn Gln Thr Ile Ile Ala Gly Met Gly Glu Leu
    450                 455                 460

His Leu Asp Ile Ile Val Asp Arg Met Lys Arg Glu Phe Asn Val Glu
465                 470                 475                 480

Ala Asn Val Gly Lys Pro Gln Val Ala Tyr Arg Glu Thr Ile Arg Gln
```

```
            485                 490                 495
Lys Val Thr Asp Val Glu Gly Lys His Ala Lys Gln Ser Gly Gly Arg
            500                 505                 510

Gly Gln Tyr Gly His Val Val Ile Asp Met Tyr Pro Leu Glu Pro Gly
            515                 520                 525

Ser Asn Pro Lys Gly Tyr Glu Phe Ile Asn Asp Ile Lys Gly Gly Val
            530                 535                 540

Ile Pro Gly Glu Tyr Ile Pro Ala Val Asp Lys Gly Ile Gln Glu Gln
545                 550                 555                 560

Leu Lys Ala Gly Pro Leu Ala Gly Tyr Pro Val Val Asp Met Gly Ile
            565                 570                 575

Arg Leu His Phe Gly Ser Tyr His Asp Val Asp Ser Ser Glu Leu Ala
            580                 585                 590

Phe Lys Leu Ala Ala Ser Ile Ala Phe Lys Glu Gly Phe Lys Lys Ala
            595                 600                 605

Lys Pro Val Leu Leu Glu Pro Ile Met Lys Val Glu Val Glu Thr Pro
            610                 615                 620

Glu Glu Asn Thr Gly Asp Val Ile Gly Asp Leu Ser Arg Arg Arg Gly
625                 630                 635                 640

Met Leu Lys Gly Gln Glu Ser Glu Val Thr Gly Val Lys Ile His Ala
            645                 650                 655

Glu Val Pro Leu Ser Glu Met Phe Gly Tyr Ala Thr Gln Leu Arg Ser
            660                 665                 670

Leu Thr Lys Gly Arg Ala Ser Tyr Thr Met Glu Phe Leu Lys Tyr Asp
            675                 680                 685

Glu Ala Pro Ser Asn Val Ala Gln Ala Val Ile Glu Ala Arg Gly Lys
            690                 695                 700

<210> SEQ ID NO 15
<211> LENGTH: 33
<212> TYPE: PRT
<213> ORGANISM: Shigella flexneri

<400> SEQUENCE: 15

Ser Leu Thr Lys Gly Arg Ala Ser Tyr Thr Met Glu Phe Leu Lys Tyr
1               5                   10                  15

Asp Glu Ala Pro Ser Asn Val Ala Gln Ala Val Ile Glu Ala Arg Gly
            20                  25                  30

Lys

<210> SEQ ID NO 16
<211> LENGTH: 33
<212> TYPE: PRT
<213> ORGANISM: Bacterioides fragilis

<400> SEQUENCE: 16

Ser Leu Thr Gly Gly Arg Ala Ser Phe Ile Met Lys Phe Ala Ser Tyr
1               5                   10                  15

Glu Leu Val Pro Ser Asp Val Gln Asp Lys Leu Ile Lys Asp Phe Glu
            20                  25                  30

Ser

<210> SEQ ID NO 17
<211> LENGTH: 33
<212> TYPE: PRT
<213> ORGANISM: Bacterioides thetaiotamicron

<400> SEQUENCE: 17
```

-continued

```
Ser Leu Thr Gly Gly Arg Ala Ser Phe Ile Met Lys Phe Ala Ser Tyr
1               5                   10                  15

Glu Leu Val Pro Thr Asp Val Gln Asp Lys Leu Ile Lys Asp Phe Glu
            20                  25                  30

Ala
```

```
<210> SEQ ID NO 18
<211> LENGTH: 33
<212> TYPE: PRT
<213> ORGANISM: unknown
<220> FEATURE:
<223> OTHER INFORMATION: Consensus of EF-G sequence from various
      elongation factors corresponding to MECO-1. Included are only
      amino acids where there are at least 2 among the sequences
      compared.
<220> FEATURE:
<221> NAME/KEY: misc_feature
<222> LOCATION: (2)..(2)
<223> OTHER INFORMATION: X = L or Q
<220> FEATURE:
<221> NAME/KEY: misc_feature
<222> LOCATION: (4)..(4)
<223> OTHER INFORMATION: X = K, Q or G
<220> FEATURE:
<221> NAME/KEY: misc_feature
<222> LOCATION: (8)..(8)
<223> OTHER INFORMATION: X = S or T
<220> FEATURE:
<221> NAME/KEY: misc_feature
<222> LOCATION: (9)..(9)
<223> OTHER INFORMATION: X = Y or F
<220> FEATURE:
<221> NAME/KEY: misc_feature
<222> LOCATION: (10)..(10)
<223> OTHER INFORMATION: X = T, S or I
<220> FEATURE:
<221> NAME/KEY: misc_feature
<222> LOCATION: (12)..(12)
<223> OTHER INFORMATION: X = E or K
<220> FEATURE:
<221> NAME/KEY: misc_feature
<222> LOCATION: (14)..(14)
<223> OTHER INFORMATION: X = L, S or A
<220> FEATURE:
<221> NAME/KEY: misc_feature
<222> LOCATION: (15)..(15)
<223> OTHER INFORMATION: X = K or S
<220> FEATURE:
<221> NAME/KEY: misc_feature
<222> LOCATION: (17)..(17)
<223> OTHER INFORMATION: X = D, N, E, A or Q
<220> FEATURE:
<221> NAME/KEY: misc_feature
<222> LOCATION: (18)..(18)
<223> OTHER INFORMATION: X = E, L or D
<220> FEATURE:
<221> NAME/KEY: misc_feature
<222> LOCATION: (19)..(19)
<223> OTHER INFORMATION: X = A or V
<220> FEATURE:
<221> NAME/KEY: misc_feature
<222> LOCATION: (21)..(21)
<223> OTHER INFORMATION: X = S, P, N, K or T
<220> FEATURE:
<221> NAME/KEY: misc_feature
<222> LOCATION: (22)..(22)
<223> OTHER INFORMATION: X = N, S or D
<220> FEATURE:
<221> NAME/KEY: misc_feature
<222> LOCATION: (23)..(23)
<223> OTHER INFORMATION: X = V or I
<220> FEATURE:
<221> NAME/KEY: misc_feature
<222> LOCATION: (24)..(24)
<223> OTHER INFORMATION: X = A or Q
<220> FEATURE:
```

```
<221> NAME/KEY: misc_feature
<222> LOCATION: (25)..(25)
<223> OTHER INFORMATION: X = Q, E or D
<220> FEATURE:
<221> NAME/KEY: misc_feature
<222> LOCATION: (26)..(26)
<223> OTHER INFORMATION: X = A or K
<220> FEATURE:
<221> NAME/KEY: misc_feature
<222> LOCATION: (27)..(27)
<223> OTHER INFORMATION: X = V, L or I
<220> FEATURE:
<221> NAME/KEY: misc_feature
<222> LOCATION: (29)..(29)
<223> OTHER INFORMATION: X = E or K
<220> FEATURE:
<221> NAME/KEY: misc_feature
<222> LOCATION: (30)..(30)
<223> OTHER INFORMATION: X = A or D
<220> FEATURE:
<221> NAME/KEY: misc_feature
<222> LOCATION: (31)..(31)
<223> OTHER INFORMATION: X = R or F
<220> FEATURE:
<221> NAME/KEY: misc_feature
<222> LOCATION: (32)..(32)
<223> OTHER INFORMATION: X = G or E

<400> SEQUENCE: 18

Ser Xaa Thr Xaa Gly Arg Ala Xaa Xaa Xaa Met Xaa Phe Xaa Xaa Tyr
1               5                   10                  15

Xaa Xaa Xaa Pro Xaa Xaa Xaa Xaa Xaa Xaa Ile Xaa Xaa Xaa Xaa
            20                  25                  30

Lys

<210> SEQ ID NO 19
<211> LENGTH: 11
<212> TYPE: PRT
<213> ORGANISM: unknown
<220> FEATURE:
<223> OTHER INFORMATION: mammalian melanocortin gamma-MSH

<400> SEQUENCE: 19

Tyr Val Met Gly His Phe Arg Trp Asp Arg Phe
1               5                   10

<210> SEQ ID NO 20
<211> LENGTH: 22
<212> TYPE: PRT
<213> ORGANISM: unknown
<220> FEATURE:
<223> OTHER INFORMATION: mammalian melanocortin beta-MSH

<400> SEQUENCE: 20

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 21
<211> LENGTH: 13
<212> TYPE: PRT
<213> ORGANISM: unknown
<220> FEATURE:
<223> OTHER INFORMATION: mammalian melanocortin alpha-MSH

<400> SEQUENCE: 21

Ser Tyr Ser Met Glu His Phe Arg Trp Gly Lys Pro Val
1               5                   10
```

```
<210> SEQ ID NO 22
<211> LENGTH: 39
<212> TYPE: PRT
<213> ORGANISM: unknown
<220> FEATURE:
<223> OTHER INFORMATION: mammalian melanocortin ACTH (1-39)

<400> SEQUENCE: 22

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 23
<211> LENGTH: 10
<212> TYPE: PRT
<213> ORGANISM: Bacteroides fragilis

<400> SEQUENCE: 23

Gln Asp Lys Leu Ile Lys Asp Phe Glu Ser
1               5                   10

<210> SEQ ID NO 24
<211> LENGTH: 15
<212> TYPE: PRT
<213> ORGANISM: Bacteroides thetaiotamicron

<400> SEQUENCE: 24

Gln Asp Lys Leu Ile Lys Asp Phe Glu Ala Lys Gln Thr Glu Glu
1               5                   10                  15
```